(12) United States Patent
Jeong et al.

(10) Patent No.: US 11,154,232 B2
(45) Date of Patent: Oct. 26, 2021

(54) MECHANO-ACOUSTIC SENSING DEVICES AND METHODS

(71) Applicants: The Regents of the University of Colorado, Denver, CO (US); The Board of Trustees of the University of Illinois, Urbana, IL (US)

(72) Inventors: Jae-Woong Jeong, Broomfield, CO (US); John Rogers, Wilmette, IL (US); Yu Hao Liu, Union City, CA (US)

(73) Assignees: THE BOARD OF TRUSTEES OF THE UNIVERSITY OF ILLINOIS, Urbana, IL (US); THE REGENTS OF THE UNIVERSITY OF COLORADO, Denver, CO (US)

( * ) Notice: Subject to any disclaimer, the term of this patent is extended or adjusted under 35 U.S.C. 154(b) by 110 days.

(21) Appl. No.: 16/190,958

(22) Filed: Nov. 14, 2018

(65) Prior Publication Data

US 2019/0150771 A1     May 23, 2019

Related U.S. Application Data

(60) Provisional application No. 62/585,894, filed on Nov. 14, 2017.

(51) Int. Cl.
*A61B 5/0432* (2006.01)
*A61B 5/333* (2021.01)
(Continued)

(52) U.S. Cl.
CPC ............ *A61B 5/333* (2021.01); *A61B 5/0006* (2013.01); *A61B 5/0024* (2013.01); *A61B 5/25* (2021.01);
(Continued)

(58) Field of Classification Search
USPC .................................................. 600/508–509
See application file for complete search history.

(56) References Cited

U.S. PATENT DOCUMENTS

2011/0213271 A1* 9/2011 Telfort ................... A61B 7/003
600/586
2013/0041235 A1 2/2013 Rodgers et al.
(Continued)

FOREIGN PATENT DOCUMENTS

KR     20160050592 A     5/2016
WO     2018/136462 A1    7/2018

OTHER PUBLICATIONS

Hattori et al., "Multifunction Skin-Like Electronics for Quantitative, Clinical Monitoring of Cutaneous Wound Healing," *Advanced Healthcare Materials*, 3 (2014) pp. 1597-1607.
(Continued)

*Primary Examiner* — Nicole F Lavert
(74) *Attorney, Agent, or Firm* — Crowell & Moring LLP

(57) ABSTRACT

Various embodiments of the present technology include a soft, conformal class of device configured specifically for mechano-acoustic recording from the skin, capable of being used on nearly any part of the body, in forms that maximize detectable signals and allow for multimodal operation, such as electrophysiological recording. Some embodiments can be configured for use in cardiovascular diagnostics, implantable device diagnostics, and human-machine interfaces (HMIs). In some embodiments, a conformal sensing device for measuring mechano-acoustic recording from skin of a human subject can include a mechano-acoustic sensor, a wireless transmitter, a flexible housing, and/or one or more electrodes.

12 Claims, 34 Drawing Sheets

(51) Int. Cl.
*A61B 5/00* (2006.01)
*G06F 3/16* (2006.01)
*A61B 7/04* (2006.01)
*A61B 5/25* (2021.01)
*A61B 5/11* (2006.01)
*G10L 15/00* (2013.01)
*A61B 5/389* (2021.01)

(52) U.S. Cl.
CPC .............. *A61B 7/04* (2013.01); *G06F 3/167* (2013.01); *A61B 5/1102* (2013.01); *A61B 5/389* (2021.01); *A61B 5/6822* (2013.01); *A61B 5/6833* (2013.01); *A61B 5/7257* (2013.01); *A61B 5/7475* (2013.01); *A61B 2562/0204* (2013.01); *G10L 15/00* (2013.01)

(56) References Cited

U.S. PATENT DOCUMENTS

| | | | |
|---|---|---|---|
| 2014/0221849 A1 | 8/2014 | Farringdon et al. | |
| 2014/0303452 A1* | 10/2014 | Ghaffari | A61B 5/03 600/301 |
| 2015/0373831 A1 | 12/2015 | Rodgers et al. | |
| 2016/0051195 A1* | 2/2016 | Pang | A61B 5/02055 600/301 |
| 2016/0066789 A1* | 3/2016 | Rogers | A61N 1/05 604/20 |
| 2017/0224257 A1 | 8/2017 | Rodgers | |
| 2017/0231571 A1 | 8/2017 | Rodgers et al. | |
| 2017/0365557 A1 | 12/2017 | Rodgers et al. | |
| 2018/0014734 A1 | 1/2018 | Rodgers et al. | |

OTHER PUBLICATIONS

Jang et al., "Rugged and breathable forms of stretchable electronics with adherent composite substrates for transcutaneous monitoring," *Nature Communications*, 15:4779 (2014) pp. 1-10.

Jeong et al., "Capacitive Epidermal Electronics for Electrically Safe, Long-Term Electrophysiological Measurements," *Advanced Healthcare Materials*, 3 (2014) pp. 642-648.

Jeong et al., "Materials and Optimized Designs for Human-Machine Interfaces via Epidermal Electronics," *Advanced Materials*, 25 (2013) pp. 6839-6846.

Lacour et al., "Stretchable Interconnects for Elastic Electronic Surfaces," *Proceedings of the IEEE*, 93:8 (2005) pp. 1459-1467.

Lee et al., "Soft Core/Shell Packages for Stretchable Electronics," *Advanced Functional Materials*, 25 (2015) pp. 3698-3704.

Liu et al., "Epidermal mechano-acoustic sensing electronics for cardiovascular diagnostics and human-machine interfaces," *Science Advances*, vol. 2 (2016) pp. 1-12.

Norton et al., "Soft, curved electrode systems capable of integration on the auricle as a persistent brain-computer interface," *PNAS*, 112:13 (Mar. 31, 2015) pp. 3920-3925.

* cited by examiner

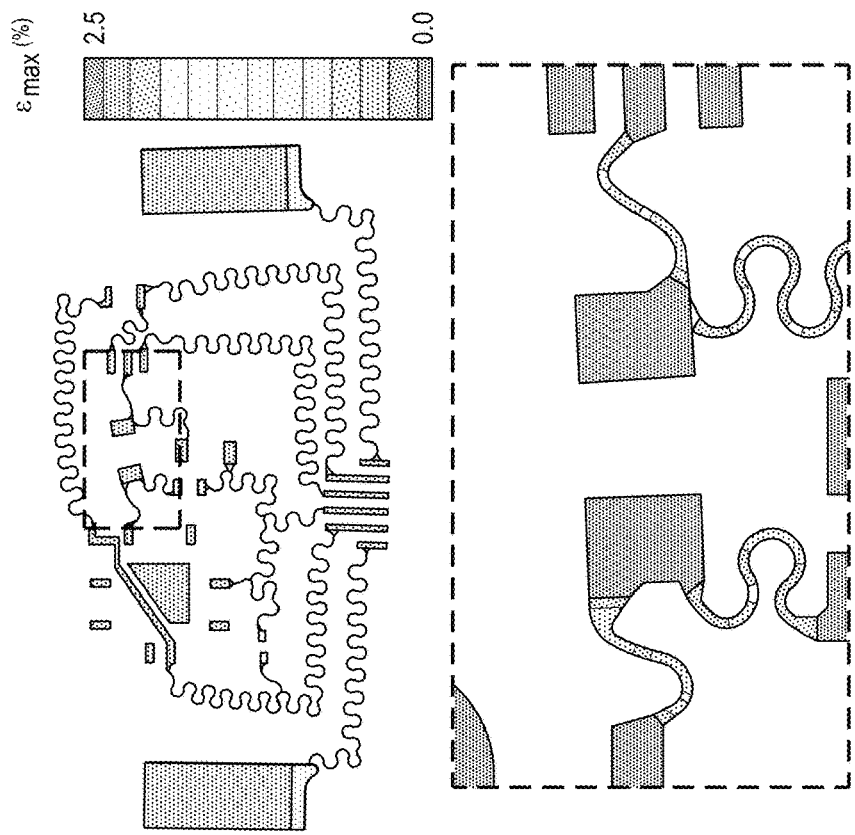
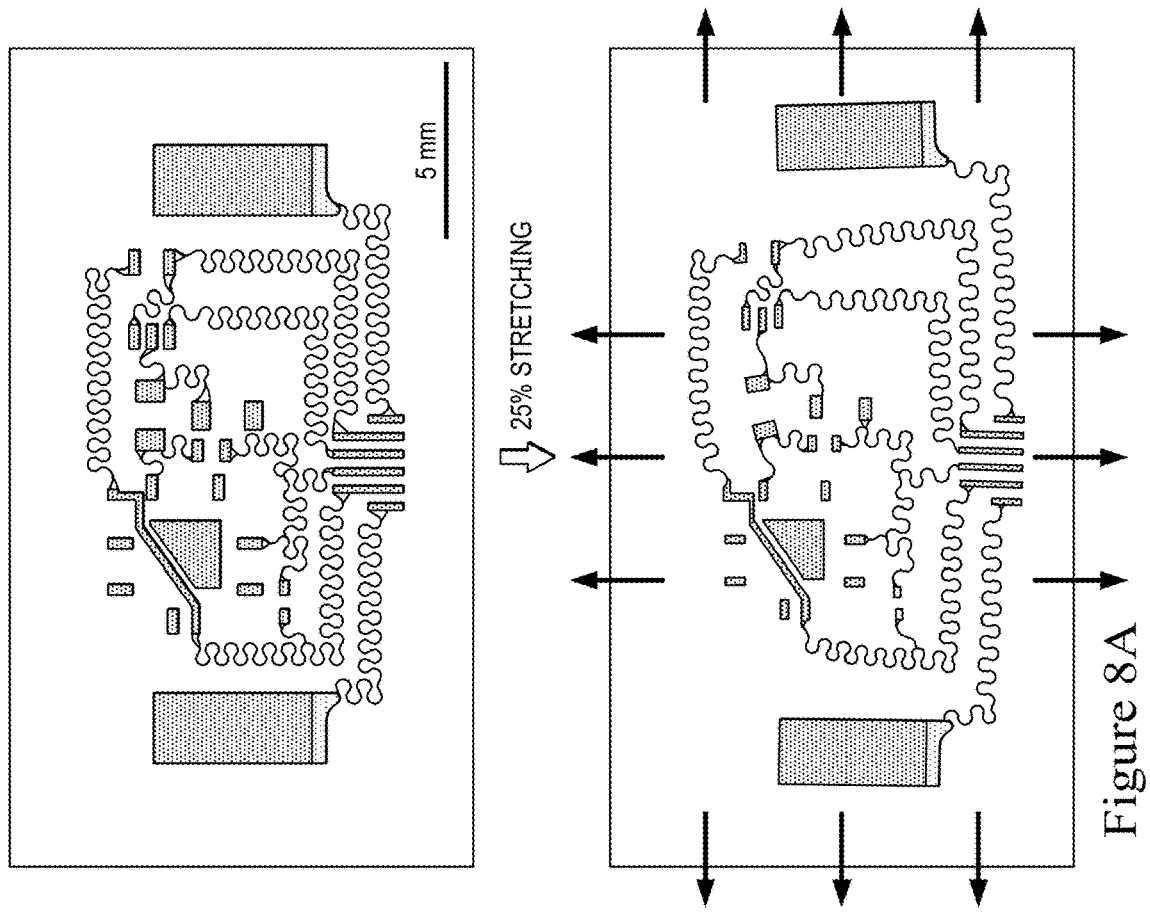
Figure 8A
Figure 8B

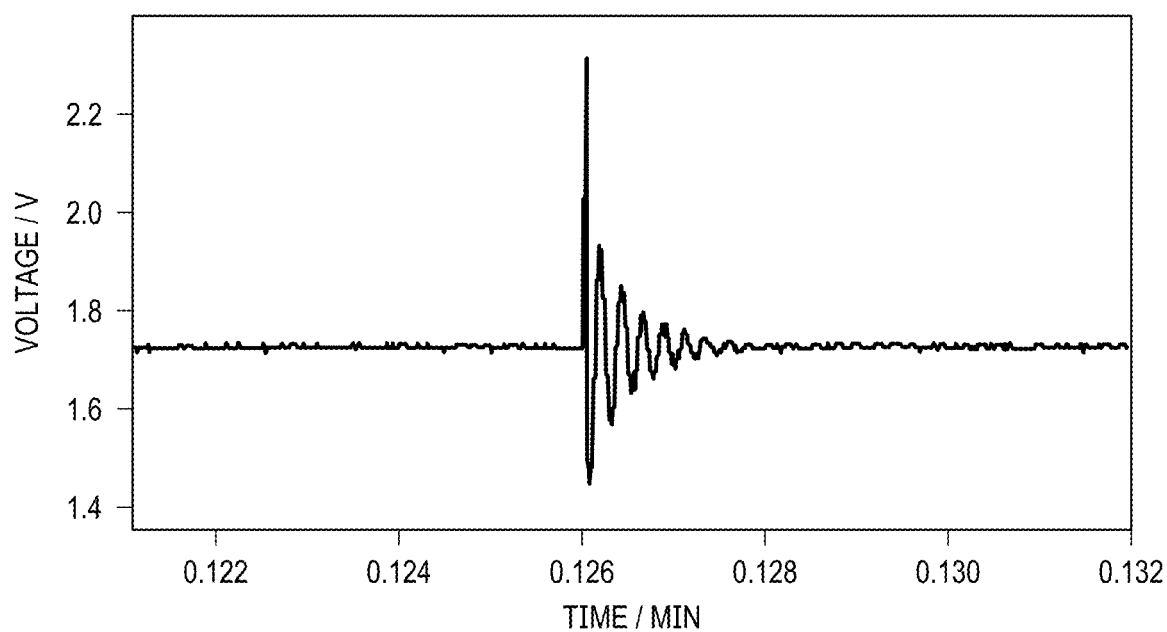
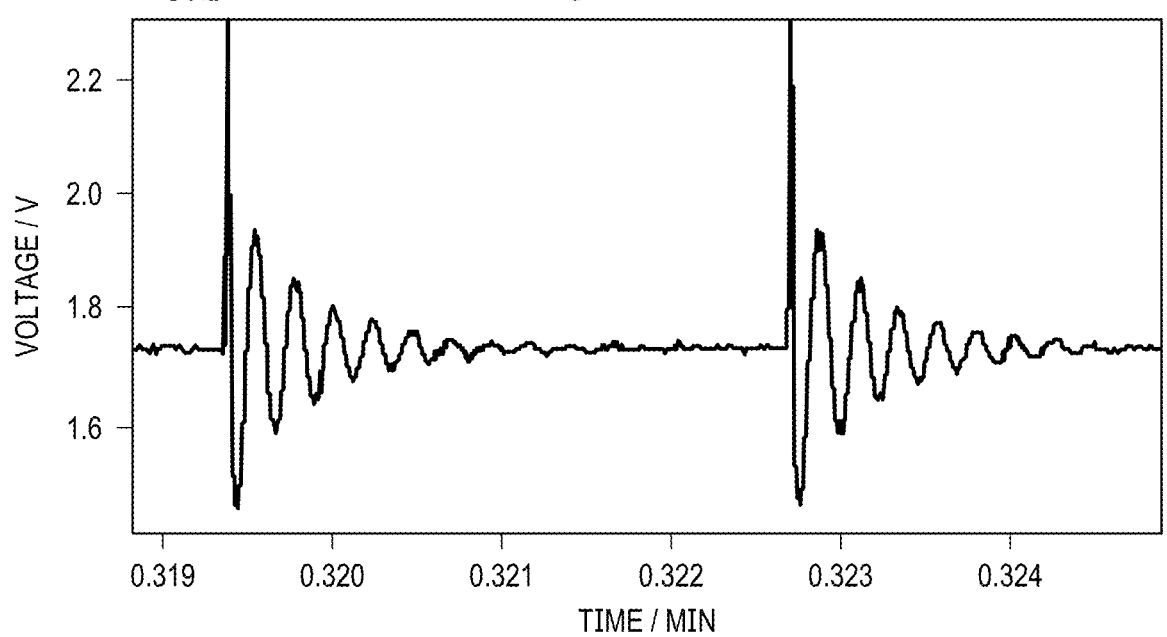

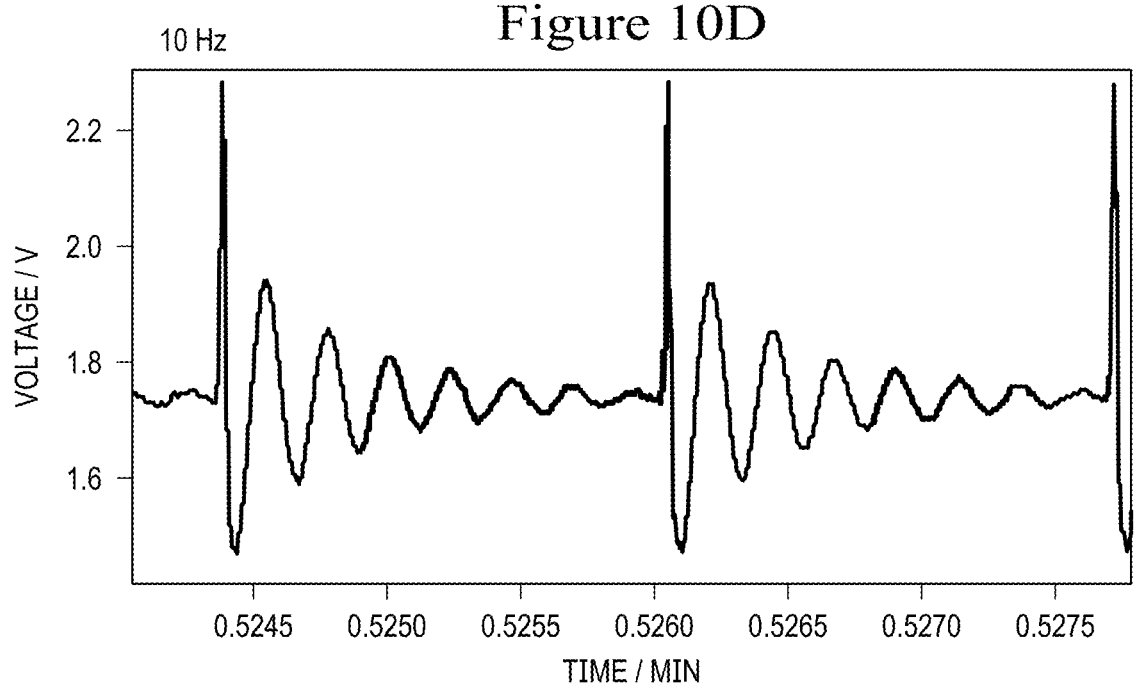
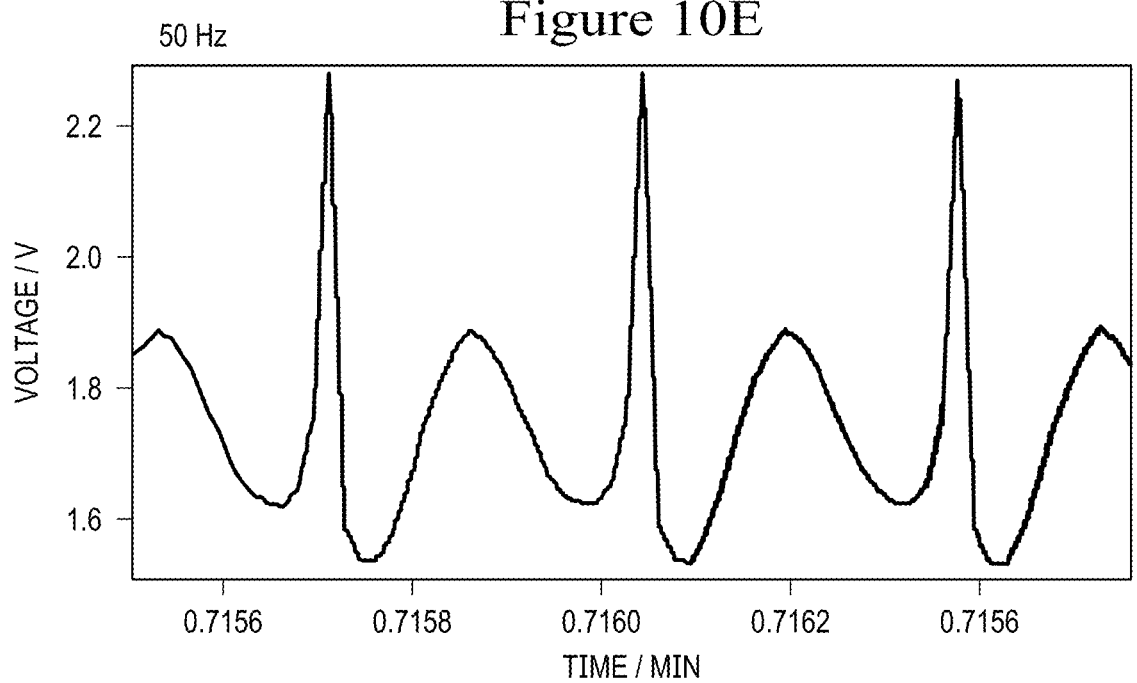

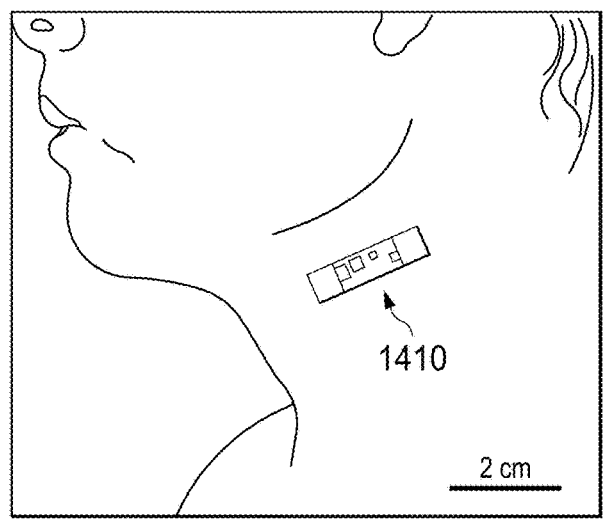
Figure 14A
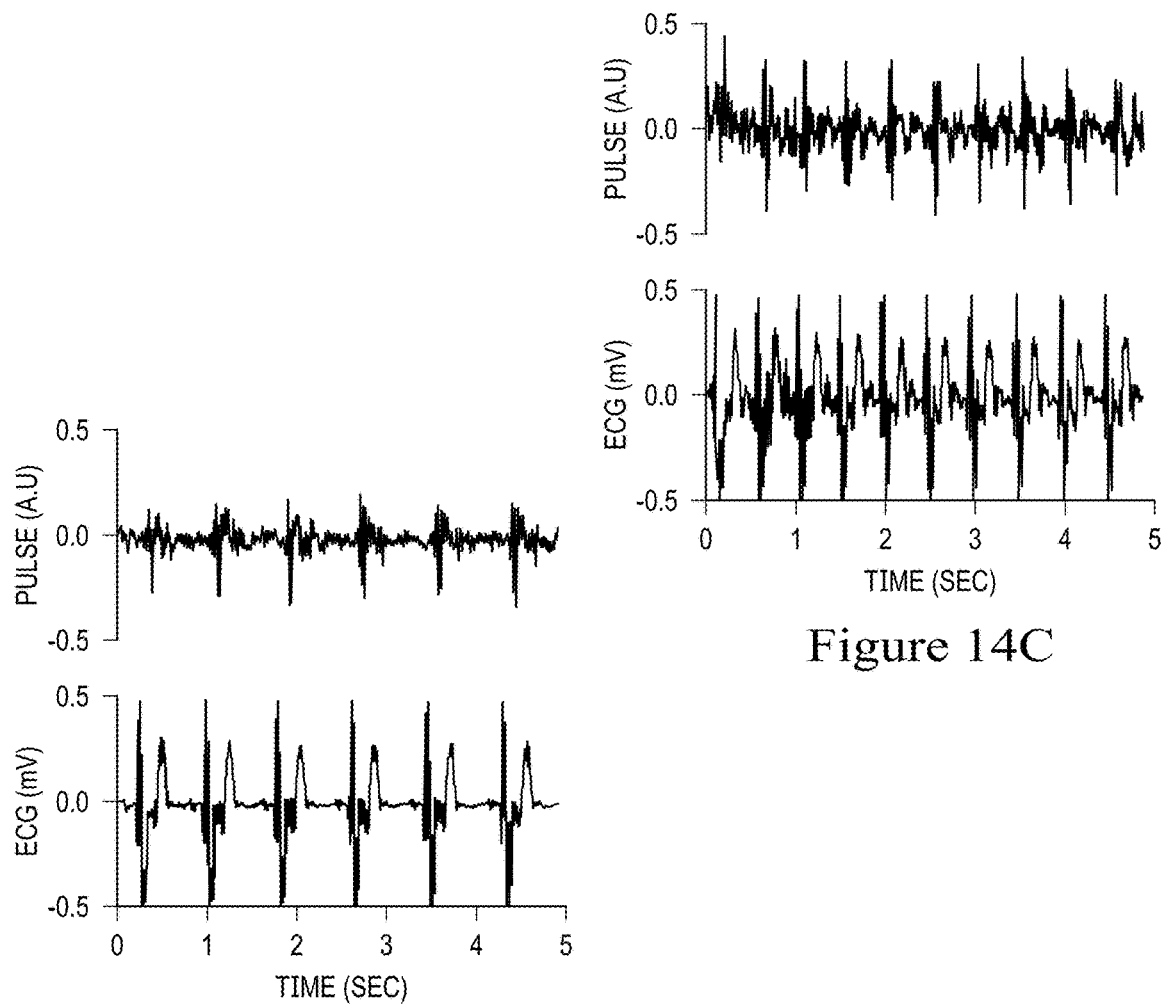
Figure 14C
Figure 14B

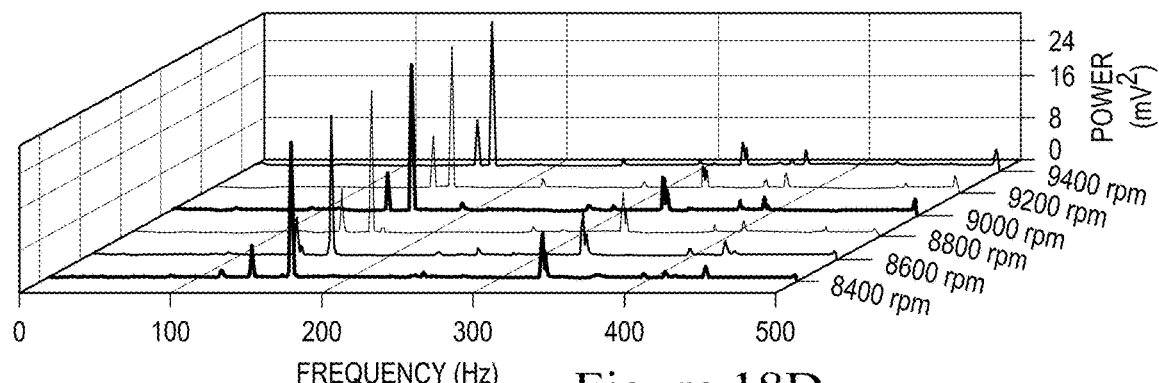
Figure 18D
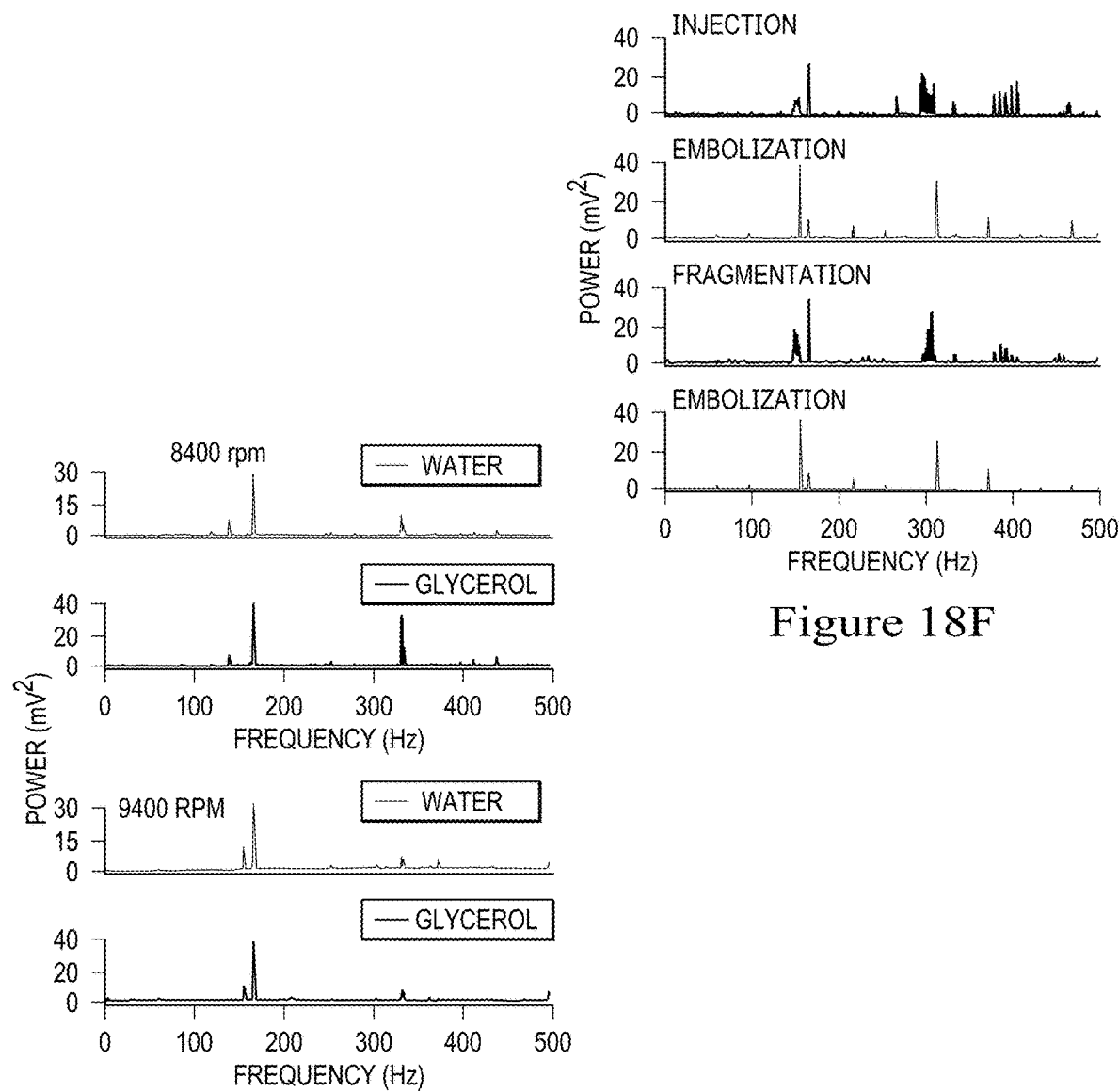
Figure 18F
Figure 18E

MECHANO-ACOUSTIC SENSING DEVICES AND METHODS

CROSS-REFERENCE TO RELATED APPLICATIONS

This application claims priority to U.S. Provisional Patent Application No. 62/585,894 filed Nov. 14, 2017, which is incorporated herein by reference in its entirety for all purposes.

TECHNICAL FIELD

Various embodiments of the present technology generally relate to mechano-acoustic sensing electronics. More specifically, some embodiments of the present technology relate to systems and methods for mechano-acoustic-electrophysiological sensing electronics configured for use in cardiovascular diagnostics, implantable device diagnostics, human-machine interfaces (HMIs), and internal medicine.

BACKGROUND

Mechano-acoustic signals are known to contain essential information for clinical diagnosis and healthcare applications. Specifically, mechanical waves that propagate through the tissues and fluids of the body as a result of natural physiological activity reveal characteristic signatures of individual events, such as the closure of heart valves, the contraction of skeletal muscles, the vibration of the vocal folds, and movement in the gastrointestinal tract. Frequencies of these signals could range from a fraction of 1 Hz (e.g., respiratory rate) to 1000 Hz (e.g., speech), often with low amplitudes beyond hearing threshold. Physiological auscultation typically occurs with analog or digital stethoscopes, in individual procedures conducted during clinical examinations.

An alternative approach relies on accelerometers in conventional, rigid electronic packages, typically strapped physically to the body to provide the necessary mechanical coupling. Research demonstrations include recording of phonocardiography (PCG; sounds from the heart), seismocardiography (SCG; vibrations of the chest induced by the beating of the heart), ballistocardiography (BCG; recoil motions associated with reactions to cardiovascular pressure), and sounds associated with respiration.

In the context of cardiovascular health, these measurements yield important insights that complement those inferred from electrocardiography (ECG). For example, structural defects in heart valves manifest as mechano-acoustic responses and do not appear directly in ECG traces. Previously reported digital measurement methods are useful for laboratory and clinical studies but (i) their form factors (rigid designs and large size, for example, 150 mm×70 mm×25 mm) limit the choices in mounting locations and prohibit their practical utility as wearable; (ii) their bulk construction involves physical masses that suppress, through inertial effects, subtle motions associated with important physiological events; (iii) their mass densities and moduli are dissimilar from those of the skin, thereby leading to acoustic impedance mismatches with the skin; and (iv) they offer only a single mode of operation, without the ability, for example, to simultaneously capture ECG and PCG/SCG/BCG signals.

SUMMARY

Systems and methods are described for mechano-acoustic sensing electronics. More specifically, some embodiments of the present technology relate to systems and methods for mechano-acoustic-electrophysiological sensing electronics configured for use in cardiovascular diagnostics, implantable device diagnostics, and human-machine interfaces (HMIs). In some embodiments, a conformal sensing device for measuring mechano-acoustic recording from skin of a human subject can include a mechano-acoustic sensor, a wireless transmitter, a flexible housing, and/or one or more capacitive electrodes.

The mechano-acoustic sensor can record mechano-acoustic signals generated by a body of a human subject or mechanically active implant. Examples of signals that can be recorded include, but are not limited to, temperature, electrophysiological signals, measurement of skin stiffness, quasi-static or dynamic dimensional changes, voice of the human subject, and the like. The mechano-acoustic sensor is configured to detect mechano-acoustic signals between 0.01 hertz and ten-thousand hertz, or a limited spectrum of frequencies within 0.01 hertz and ten-thousand hertz. The wireless transmitter can be configured to wirelessly transmit (e.g., via Bluetooth) the mechano-acoustic signals to an external monitoring device. The flexible housing can be configured to encapsulate the mechano-acoustic sensor and wireless transmitter.

In some embodiments, the flexible housing can include an affixation mechanism to allow conformal integration of the conformal sensing device with curvilinear regions of the skin of the human subject. In some embodiments, the conformal sensing device can have a mass less than five grams and a thickness less than ten millimeters. The flexible housing can include an upper flexible insulating layer, a lower flexible insulating layer, and an elastomeric core that comprises an elastic material. Some embodiments can include one or more filters, integrated into the conformal sensing device or located in the external monitoring device, to receive the mechano-acoustic signals from the mechano-acoustic sensor and create processed signals from the mechano-acoustic signals. The mechano-acoustic sensor can be configured to capture both electromyogram (EMG) signals from articulator muscle groups and acoustic vibrations from vocal cords and the external monitoring device can process the electromyogram (EMG) signals from the articulator muscle groups and the acoustic vibrations from vocal cords to identify speech from the human subject.

Some embodiments provide a method for operating a speech-based human-machine interface. The method can include detecting, using a flexible epidermal sensor affixed to skin of a human, vibratory and acoustic signals. Representations of the vibratory and acoustic signals can be transmitted from the flexible epidermal sensor affixed to the skin of the human and to a human machine interface. The human machine interface can receive the representations and process the vibratory and acoustic signals to detect one or more instructions to control a machine. For example, the vibratory and acoustic signals can represent speech and the instructions detected by the human machine interface can include one or more words. As another example, the vibratory and acoustic signals can represent hand-writing and the instructions detected by the human machine interface can include one or more letters or words. In some embodiments, artificial intelligence or machine learning components and/or technique, to identify patterns within the signal and/or classify various detected objects within the signals. For example, some embodiments may use support vector machines, k-means, deep neural networks classifiers, artificial neural networks, supervised learning, unsupervised learning, reinforcement learning, and the like.

Embodiments of the present invention also include computer-readable storage media containing sets of instructions to cause one or more processors to perform the methods, variations of the methods, and other operations described herein.

In some embodiments a device can include a sensing circuit, an ultralow-modulus elastomeric core, and a layer of low-modulus silicone. The sensing circuit can include a mechano-acoustic sensor configured to detect vibratory, acoustic and/or mechanical signals generated by a human subject or implanted medical device. The ultralow-modulus elastomeric core can be configured to encapsulate the sensing circuit. The layer of low-modulus silicone can be placed above and below the ultralow-modulus elastomeric core. In some embodiments, the layer of low-modulus elastomer can be configured to function as an interface to skin of a human subject. In some embodiments, the device can have a mass less than five grams and a thickness less than ten millimeters. The mechano-acoustic sensor can be configured to detect mechano-acoustic signals between 0.01 hertz and ten-thousand hertz, or a limited spectrum of frequencies within 0.01 hertz and ten-thousand hertz.

While multiple embodiments are disclosed, still other embodiments of the present invention will become apparent to those skilled in the art from the following detailed description, which shows and describes illustrative embodiments of the invention. Embodiments of the present technology will be described and explained through the use of the accompanying drawings.

BRIEF DESCRIPTION OF THE DRAWINGS

Embodiments of the present technology will be described and explained through the use of the accompanying drawings in which:

FIGS. 8A-8B illustrate the results of a 3D-finite element analysis for a system without any of the device components subject to biaxial stretching;

FIGS. 10A-10H are plots illustrating the vibration response of the accelerometer chip without analog filters used in some embodiments, for example, FIG. 10A illustrates a vibration response with time interval between discrete testing frequencies, which FIGS. 10B-10H illustrate the vibration response at 1 Hz, 5 Hz, 10 Hz, 50 Hz, 100 Hz, 250 Hz, 500 Hz, respectively;

FIGS. 14A-14C illustrate an application of an epidermal mechano-acoustic-electrophysiological device on the neck with FIG. 14A showing optical images of sensor placed over the carotid artery, FIG. 14B showing Simultaneous measurement of ECG and pulse signal during rest, and FIG. 14C showing simultaneous measurement of ECG and pulse signal after exercise;

FIG. 18D shows a comparison of vibrational responses in a circulation loop with water and with glycerol at 8400 rpm (top) and 9400 rpm (bottom);

FIG. 18E is a demonstration of changes in acoustic signature associated with circulation of a blood clot (500 μL) in the glycerol loop during stages of initial injection of the blood clot, first few circulation passes without decomposition, subsequent complete decomposition, and circulation of tiny blood clots;

FIG. 18F is a demonstration of dominant acoustic frequencies associated with circulation of a blood clot (500 μL) during stages of initial injection of the blood clot, first few circulation passes without decomposition, subsequent complete decomposition, and circulation of tiny blood clots;

Figure 1:
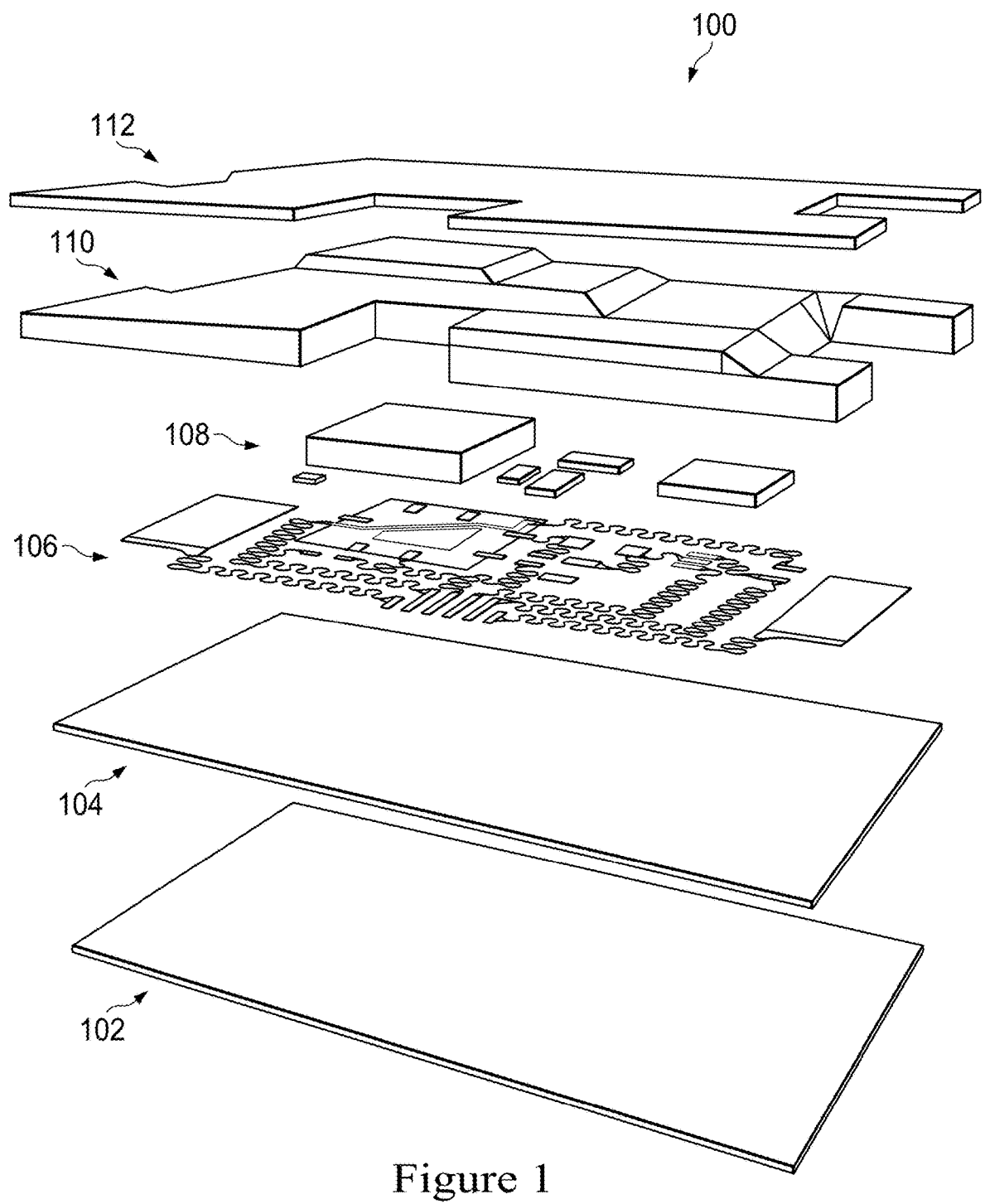
FIG. 1 illustrates an exploded view diagram of an example of an epidermal mechano-acoustic-electrophysiological measurement device according to some embodiments of the present technology.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to mechano-acoustic sensing. More specifically, some embodiments of the present technology relate systems and methods for mechano-acoustic sensing electronics that can be configured for a variety of application including, but not limited to cardiovascular diagnostics and human-machine interfaces (HMIs).

Physiological mechano-acoustic signals, often with frequencies and intensities that are beyond those associated with the audible range, provide information of great clinical utility. Stethoscopes and digital accelerometers in conventional packages can capture some relevant data, but neither is suitable for use in a continuous, wearable mode, and both have shortcomings associated with mechanical transduction of signals through the skin.

In contrast, various embodiments of the present technology include a soft, conformal class of device configured specifically for mechano-acoustic recording from the skin. Some embodiments of the device can be used on nearly any part of the body, in forms that maximize detectable signals and allow for multimodal operation, such as electrophysiological recording. Experimental and computational studies highlight the key roles of low effective modulus and low areal mass density for effective operation in this type of measurement mode on the skin. Demonstrations involving seismocardiography and heart murmur detection in a series of cardiac patients illustrate utility in advanced clinical diagnostics. Monitoring of pump thrombosis in ventricular assist devices provides an example in characterization of mechanical implants. Speech recognition and human-machine interfaces represent additional demonstrated applications. These and other possibilities suggest broad-ranging uses for soft, skin-integrated digital technologies that can capture human body acoustics.

Various embodiments provide unique electronic devices enabled by recent advances in materials science and mechanics principles can be designed with physical properties that match the soft, mechanical compliance of the skin, thereby allowing long-term (up to ~2 weeks) integration with nearly any external surface of the body, with form factors that resemble those of a temporary tattoo. These embodiments can be referred to as epidermal electronics and qualitatively expand the range of physiological measurements that are possible in wearable device platforms. Many of these operational modes rely critically on an intimate, physical interface to the skin. Examples include precision measurement of temperature and thermal transport characteristics, recording of electrophysiological processes and variations in electrical impedance, characterization of skin stiffness, and monitoring of quasi-static or dynamic dimensional changes, such as those associated with swelling/deswelling or pulsatile blood flow.

In accordance with various embodiments, the electronic devices can have properties and interfaces with the skin that include low thermal and electrical contact resistances, small thermal masses, and soft, compliant mechanics. Moreover, some embodiments can be constructed with exceptionally low mass densities, approaching those of the epidermis itself. As a result, mechano-acoustic coupling of the device to the body through the skin can be highly efficient.

Various embodiments of the present technology provide a different type of mechano-acoustic-electrophysiological sensing platform that exploits the most advanced concepts in stretchable electronics to allow soft, conformal integration with the skin. The result allows precision recordings of vital physiological signals in ways that bypass many of the limitations of conventional technologies. The mechano-acoustic modality leverages miniaturized, low-power accelerometers with bandwidths tuned to essential body processes (e.g., 0.5 to 550 Hz) and associated conditioning electronics. Soft, strain-isolating core/shell packaging assemblies, together with electronics for electrophysiological recording from dry, capacitive electrodes, represent the other essential features of these stretchable systems. The resulting devices can have a mass of 213.6 mg, a thickness of 2 mm, effective moduli of 31.8 kPa (in the x direction) and 31.1 kPa (in the y direction), and bending stiffnesses of 1.02 mN m (in the x direction) and 0.94 mNm (in the y direction), which correspond to values that are orders of magnitude lower than those previously reported. The outcomes include qualitative improvements in measurement capabilities and wearability, in formats that can interface with nearly any region of the body, including curvilinear parts of the neck to capture signals associated with respiration, swallowing, and vocal utterances.

Specific data show simultaneous recording of arterial pressure variations on the neck, electrophysiology (EP) signals and SCG from the chest for systole and diastole cardiac cycles, and four auscultation sites (aortic, pulmonary, tricuspid, and mitral) for heart murmurs. Vibrational acoustics of ventricular assist devices (VADs) (that is, devices used to augment failing myocardial function, though often complicated by intradevice thrombus formation) can be captured and used to detect pump thrombosis or drive malfunction. Beyond cardiology, applications exist in speech recognition and classification for human-machine interfaces, in modes that capture vibrations of the larynx without interference from noise in the ambient environment. Baseline studies on the biocompatibility of the skin interface and on the mechanical properties and fundamental aspects of the interface coupling provide additional insights into the operation.

Various embodiments of the present technology provide for a wide range of technical effects, advantages, and/or improvements. For example, various embodiments include one or more of the following technical effects, advantages, and/or improvements: 1) unique conformal device that can be affixed to a patient for precision measurements of acoustic and vibratory signatures of body processes and of mechanically active implants; 2) low-mass (e.g., less than 250 mg) allowing for collection of vibratory signals; 3) recording of mechano-acoustic signals including, but not limited to, temperature and thermal transport characteristics, recording of electrophysiological processes and variations in electrical impedance, characterization of skin stiffness, and monitoring of quasi-static or dynamic dimensional changes, such as those associated with swelling/deswelling or pulsatile blood flow; 4) use of unconventional and non-routine computer operations to collect and analyze signals for control of machines; and/or 5) changing the manner in which a computing system reacts to human interactions.

In the following description, for the purposes of explanation, numerous specific details are set forth in order to provide a thorough understanding of embodiments of the present technology. It will be apparent, however, to one skilled in the art that embodiments of the present technology may be practiced without some of these specific details. While, for convenience, embodiments of the present technology are described with reference to cardiovascular diagnostics, the present technology provides many other uses in a wide variety of potential technical fields.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

FIG. 1 illustrates an exploded view diagram 100 of an example of an epidermal mechano-acoustic-electrophysiological measurement device according to some embodiments of the present technology. As illustrated in FIG. 1, an epidermal mechano-acoustic-electrophysiological measurement device can include a lower elastomeric shell 102, lower silicone core encapsulation 104, stretchable interconnects 106, electronic devices 108 such as accelerometers, amplifiers, resistors, capacitors, and the like, an upper silicone core encapsulation 110, and an upper elastomeric shell 112.

Some embodiments can include filamentary serpentine copper traces (e.g., 3 mm, placed at the neutral plane between layers of polyimide (PI) encapsulation (1.2 mm)) as circuit interconnects between commercial, small-scale chip components, all encapsulated above and below by an ultralow-modulus elastomeric core (e.g., Silbione RT Gel 4717 A/B, Bluestar Silicone; Young's modulus E=5 kPa (2, 37)). A thin layer of low-modulus silicone (e.g., Ecoflex, Smooth-On) (E=60 kPa) can serve as a shell 112. This core 110/shell 112 structure minimizes physical constrains on motions of the interconnects to improve stretchability, and it mechanically isolates the constituent device components to reduce stresses (and associated discomfort) at the skin interface.

Openings in this structure used in various embodiments can provide access to contact pads to attach a pair of electrophysiological measurement electrodes (e.g., Au, 200 nm) and a thin cable connection (e.g., 100 mm; anisotropic conductive film (ACF), Elform) to an external data acquisition system (not shown). The result is a soft, skin-compatible device platform that can accommodate significant levels of deformation without altering the operation. The direct mechanical interface to the skin, the robustness of adhesion that follows from the low-modulus construction, the low total mass, and the multifunctional operation represent key distinguishing features over previously reported wearable accelerometers.

Figure 2:
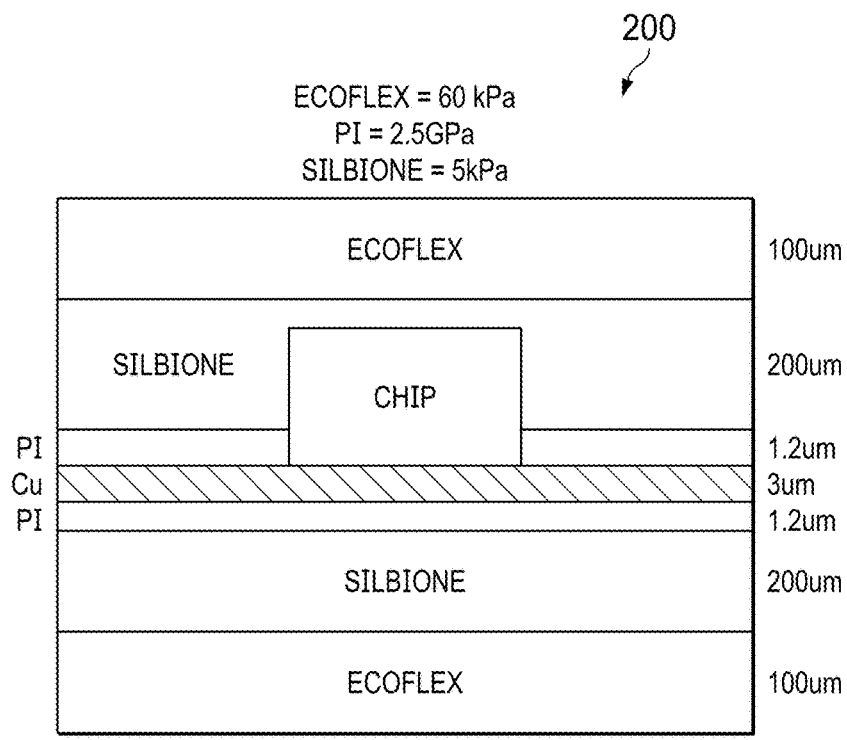
FIG. 2 illustrates a device cross-section of an example of an epidermal mechano-acoustic-electrophysiological measurement device according to some embodiments of the present technology including materials thickness and elastic modulus information.

In accordance with various embodiments, the lower elastomeric shell 102 can include a 100 um layer of Ecoflex having a modulus of 60 kPa. The lower silicone core encapsulation 104 can include a 200 um layer of Silbione having a modulus of 5 kPa. The stretchable interconnects 106 can include serpentine copper traces 3 um thick sandwiched between two 1.2 um layers of polyimide (PI) having a modulus of 2.5 GPa. The electronic devices 108 can be bonded to the stretchable interconnects 106, then covered with the upper silicone core encapsulation 110 which includes a 200 um layer of Silbione. The upper elastomeric shell 112 can include a 100 um layer of Ecoflex. FIG. 2 illustrates a device cross-section 200 of an example of an epidermal mechano-acoustic-electrophysiological measurement device according to some embodiments of the present technology including thickness and modulus information.

Various embodiments can use a variety of materials and structures that lead to the type of soft mechanics, water-permeable, and adhesive, biocompatible surfaces needed for comfortable, robust, long-lived integration on the skin. For example, some embodiment can include an additional base layer of Silbione on the bottom shell surface can provide adequate adhesive force (e.g., 1.16 kPa) for nondestructive and reversible attachment to skin. Measurements of the water vapor permeability of Silbione, in combination with previously reported results of Ecoflex, demonstrate that the core/shell encapsulation layer has a water vapor transmission loss rate that is similar to that of widely used medical dressings (e.g., Tegaderm, 3M Medical).

Cytotoxicity tests that involve culturing mouse embryonic fibroblasts (MEFs) on the surfaces of the device for five days demonstrate biocompatibility. Specifically, cells spread uniformly over the samples and remain attached for the duration of the assay, with no observable signs of apoptosis or necrosis. Visualizing cells at 1-, 3-, and 5-day time points by staining with calcein AM and ethidium homodimer-1 indicates >95% viability after 5 days.

The fabrication process used in various embodiments can involve three parts: (i) patterning of the circuit interconnects; (ii) transfer-printing and chip-bonding onto a soft, core/shell substrate; and (iii) covering the top surface with a similar soft core/shell structure.

Fabrication of the interconnects can begin with a commercial laminate (e.g., MicroThin, Oak-Mitsui Inc.) that contains a copper carrier film (e.g., 17.5 μm) and a thin copper foil (e.g., 3 μm) separated by a release layer. Spin-coating and thermal curing formed a film of PI (e.g., 1.2 μm; PI 2545, HD MicroSystems) on the side with the thin copper foil (e.g., 3 μm). Peeling this PI-coated layer from the thick copper layer allowed its attachment onto a glass slide coated with poly(dimethylsiloxane) (e.g., sylgard 184, Dow Corning).

In some embodiments the fabrication process can include: (i) Photolithography and metal etching that defines a pattern of interconnects in the copper. Another spin-coating and curing process yields a uniform layer of PI on the resulting pattern. Photolithography and reactive ion etching (e.g., RIE, Nordson MARCH) define the top and bottom layers of PI in geometries matching those of the interconnects. (ii) A piece of watersoluble tape (e.g., Aquasol) enables the transfer of these encapsulated interconnects onto a tri-layer film supported by a silicon wafer, prepared by spin-coating (e.g., 4000 rpm) and curing a thin layer of an ultrasoft silicone (e.g., Silbione, RT Gel 4717 A/B, Bluestar Silicones), followed by a layer of slightly stiffer silicone (e.g., Ecoflex, 00-30, Smooth-On) at 1000 rpm and, finally, another layer of ultrasoft silicone at 1000 rpm.

This tri-layer defines the skin-adhesive interface and the core/shell substrate. Removal of the tape by immersion in water exposes the interconnects to allow bonding of the device components onto designated pads using solder paste (e.g., Indalloy 290, Indium Corporation) and a heat gun at ~165° C. (iii) Encapsulation begins with placement of cured, individual pieces of silicone onto the pads that connect to the ECG electrodes and to those that interface to the ACF cable. Spin-coating (e.g., 1000 rpm) and curing a layer of Silbione followed by a layer of Ecoflex at 1000 rpm defines the core/shell superstrate. Removal of the silicone pieces completes the fabrication process. Attachment of the ACF cable and ECG electrodes occurs just before mounting the device on the skin.

Figure 3:
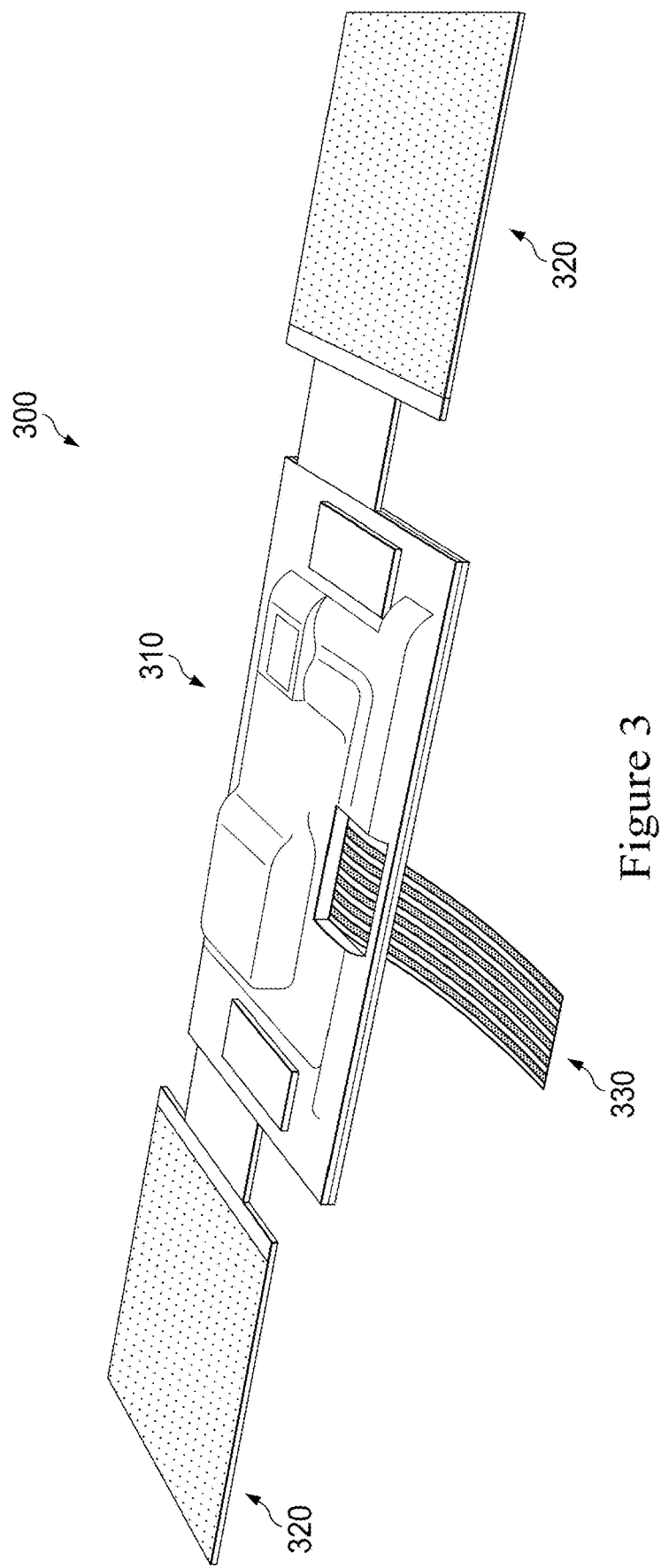
FIG. 3 illustrates an example of an epidermal mechano-acoustic-electrophysiological measurement device according to some embodiments of the present technology.

FIG. 3 illustrates an example of an epidermal mechano-acoustic-electrophysiological measurement device 300 according to some embodiments of the present technology. This example assembly includes epidermal mechano-acoustic-electrophysiological measurement device 310, along with associated electrodes 320, and anisotropic conducting film 330. The embodiments illustrated in FIG. 3 illustrate a mechano-acoustic-electrophysiological sensing platform that exploits the most advanced concepts in flexible and stretchable electronics to allow soft, conformal integration with the skin.

The technology allows precision recordings of vital physiological signals in ways that bypass many of the limitations of conventional technologies (e.g. heavy mass and bulky package). The mechano-acoustic modality includes miniaturized, low-power accelerometers with bandwidths tuned to essential body processes (e.g., 0.5 to 550 Hz) and associated conditioning electronics. Soft, strain-isolating core/shell packaging assemblies, together with electronics for electrophysiological recording from dry, capacitive electrodes, represent other example features of these stretchable systems. Example embodiments of the present technology have a mass of 213.6 mg, a thickness of 2 mm, effective moduli of 31.8 kPa (in the x direction) and 31.1 kPa (in the y direction), and bending stiffnesses of 1.02 mN m (in the x direction) and 0.94 mNm (in the y direction), which correspond to values that are orders of magnitude lower than those previously reported.

Figure 4:
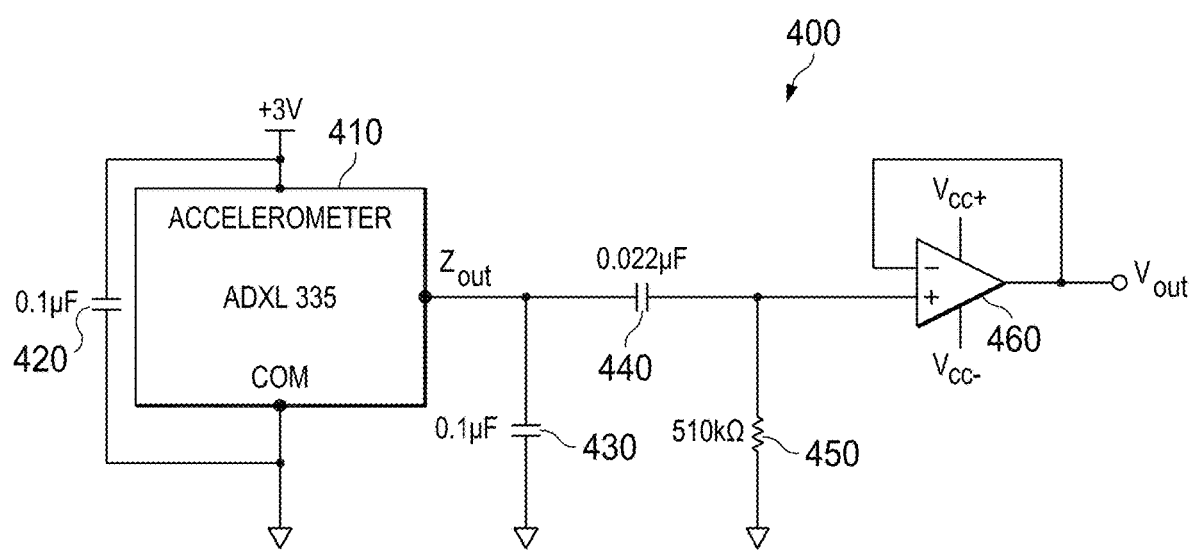
FIG. 4 illustrates a circuit diagram of an example of an epidermal mechano-acoustic-electrophysiological measurement device according to some embodiments of the present technology.

FIG. 4 illustrates a circuit diagram 400 of an example of an epidermal mechano-acoustic-electrophysiological measurement device according to some embodiments of the present technology. The sensing circuit comprises a mechano-acoustic sensor 410 (ADXL335, Analog Devices), low-pass and high-pass filters (capacitors 420, 430, and 440, and resistor 450), a preamplifier 460 (e.g., TSV991A, STMicroelectronics), and removable and reusable capacitive electrodes for EP recording. In some embodiments, the sensor 410 can have a frequency bandwidth (e.g., 0.5 to 550 Hz) that lies between the range of targeted cardiovascular sounds and speech.

For healthy adults, the first sound and the second sound of the heart have acoustic frequencies of 10 to 180 Hz and 50 to 250 Hz, respectively. Vibration frequencies of vocal folds in humans range from 90 to 2000 Hz, with an average fundamental frequency of ~116 Hz (male; mean age, 19.5), ~217 Hz (female; mean age, 19.5), and ~226 Hz (child, ages 8 to 11) during conversation. To enable sensing of cardiac operation and speech, the cutoff frequency of the low-pass filter can be 500 Hz. The high-pass filter (e.g., cutoff frequency, 15 Hz) removes motion artifacts.

Figure 5:
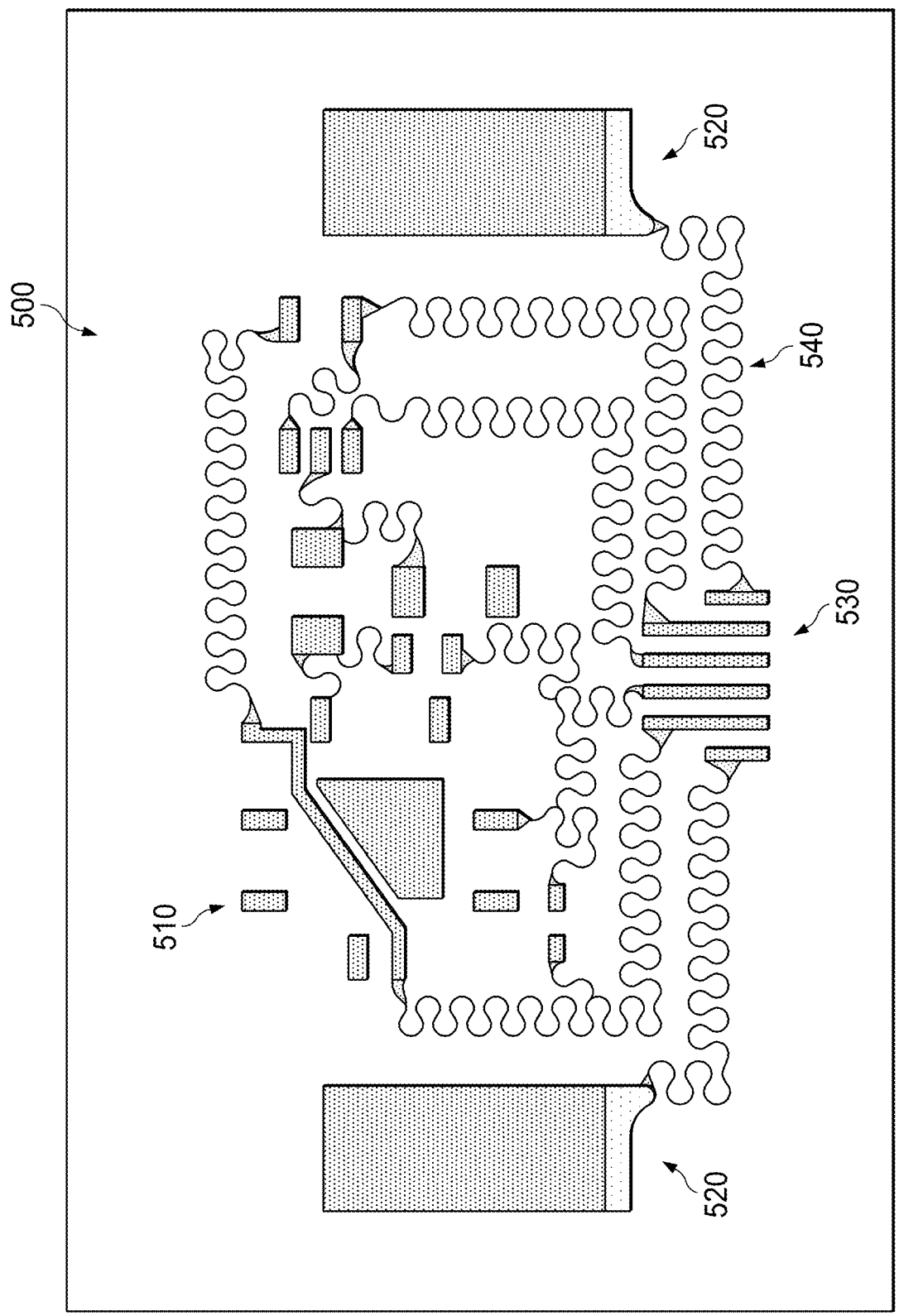
FIG. 5 illustrates a circuit layout of an example of an epidermal mechano-acoustic-electrophysiological measurement device according to some embodiments of the present technology before chip bonding.

FIG. 5 illustrates a circuit layout 500 of an example of an epidermal mechano-acoustic-electrophysiological measurement device according to some embodiments of the present technology before chip bonding. This example circuit layout 500 includes copper pads for the connection of electronic components 510, pads for the connection of electrodes 520, contacts for the connection of a cable 530, and serpentine copper connections 540 between the electronic components.

Figure 6:
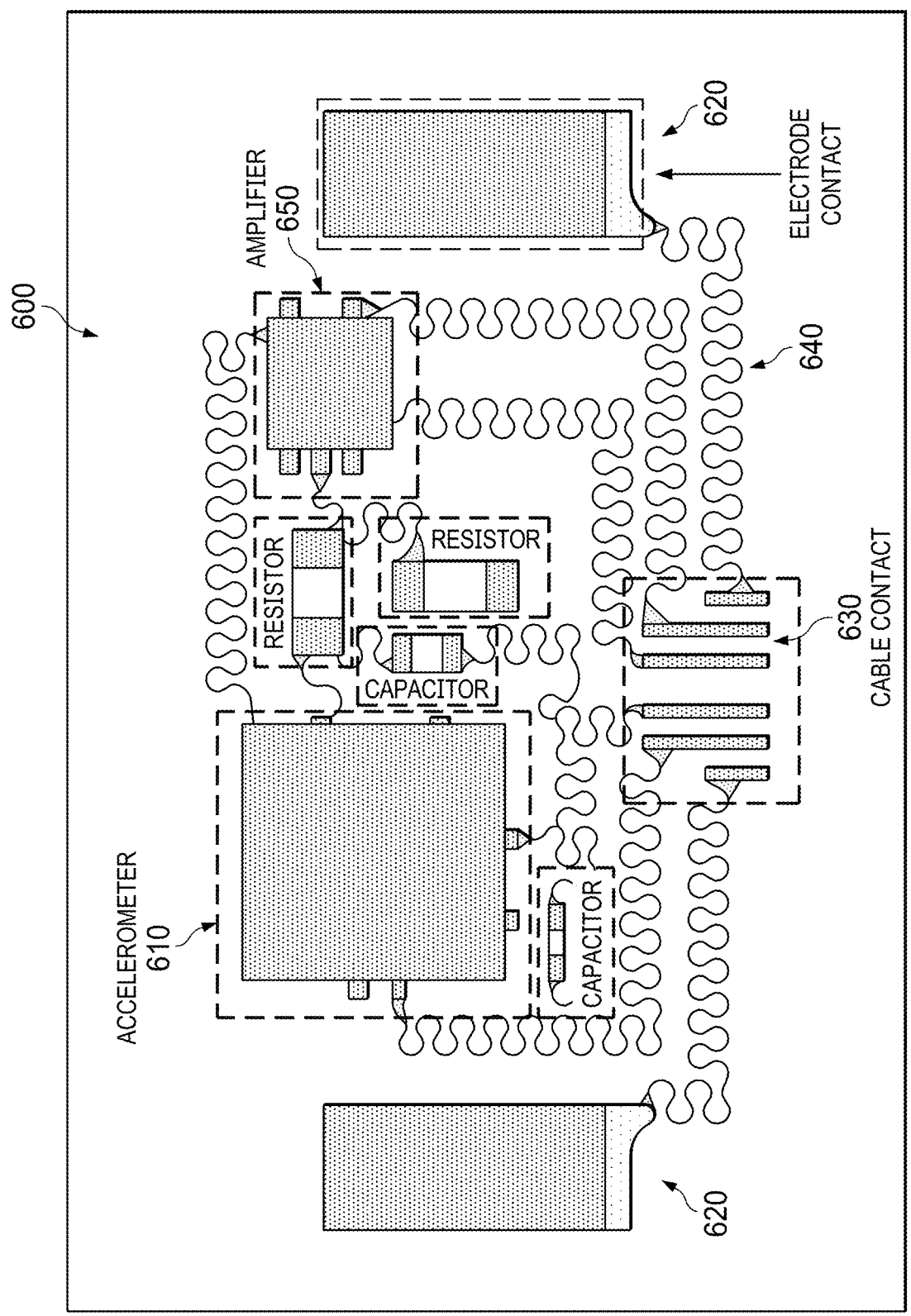
FIG. 6 illustrates a circuit layout of an example of an epidermal mechano-acoustic-electrophysiological measurement device according to some embodiments of the present technology after chip bonding.

FIG. 6 illustrates a circuit layout 600 of an example of an epidermal mechano-acoustic-electrophysiological measurement device according to some embodiments of the present technology after chip bonding. This example circuit layout 600 illustrates the circuit layout 500 of FIG. 5 after the electronic components have been bonded to the appropriate copper pads. Accelerometer 610 and amplifier 650 are illustrated along with various capacitors and resistors comprising filters. Serpentine copper connections 640 can connect the electrodes 620 and a cable 630.

Figure 7B:
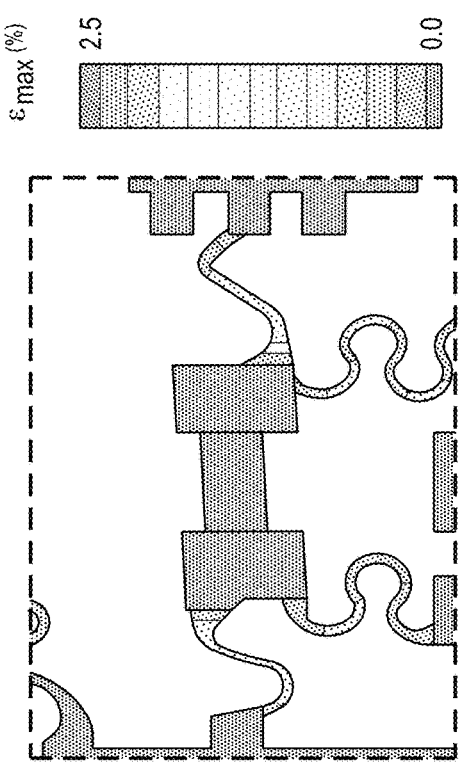
FIG. 7B is a magnified view of modeling results for the part of the interconnect structures used in some embodiments that experience the highest strain.
Figure 7A:
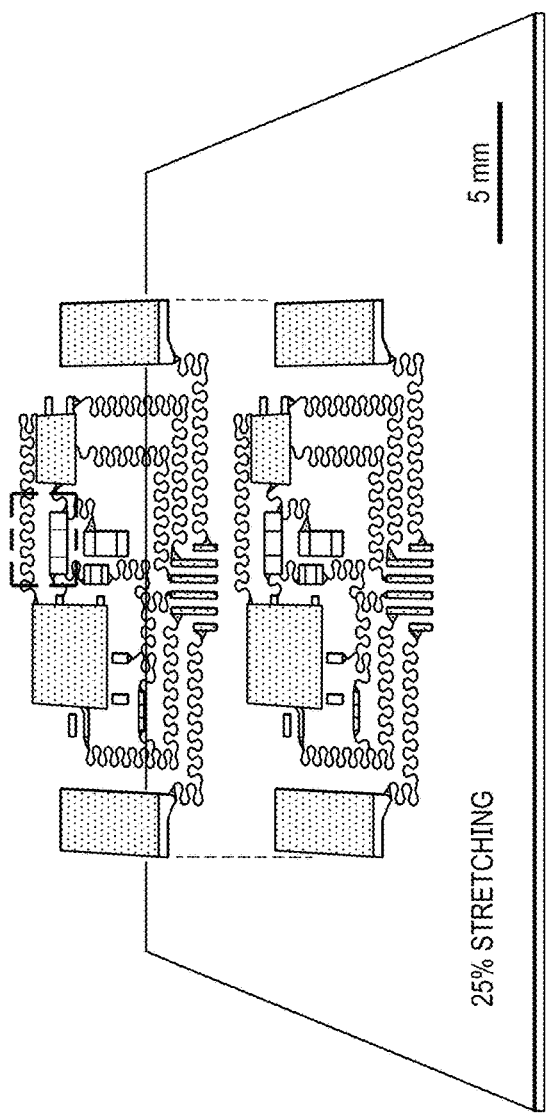
FIG. 7A provide an overlay of an optical image and finite element simulation results for a device under biaxial stretching to a strain of 25%.

Experimental studies and three-dimensional finite element analysis (3D-FEA) of the system under a biaxial strain of 25% allow for the examination of the mechanics at levels of deformation that exceed those likely to be encountered on the skin. Optical images and corresponding simulation results in FIG. 7A show good agreement. The strain contour in the upper layer of FIG. 7A indicates that the maximum principal strains in most locations are below 1%. Large strains (~2.5%), still below the fracture threshold of the PI/Cu/PI system, occur only in certain regions of the interconnects, highlighted by the red dashed box.

Figure 9:
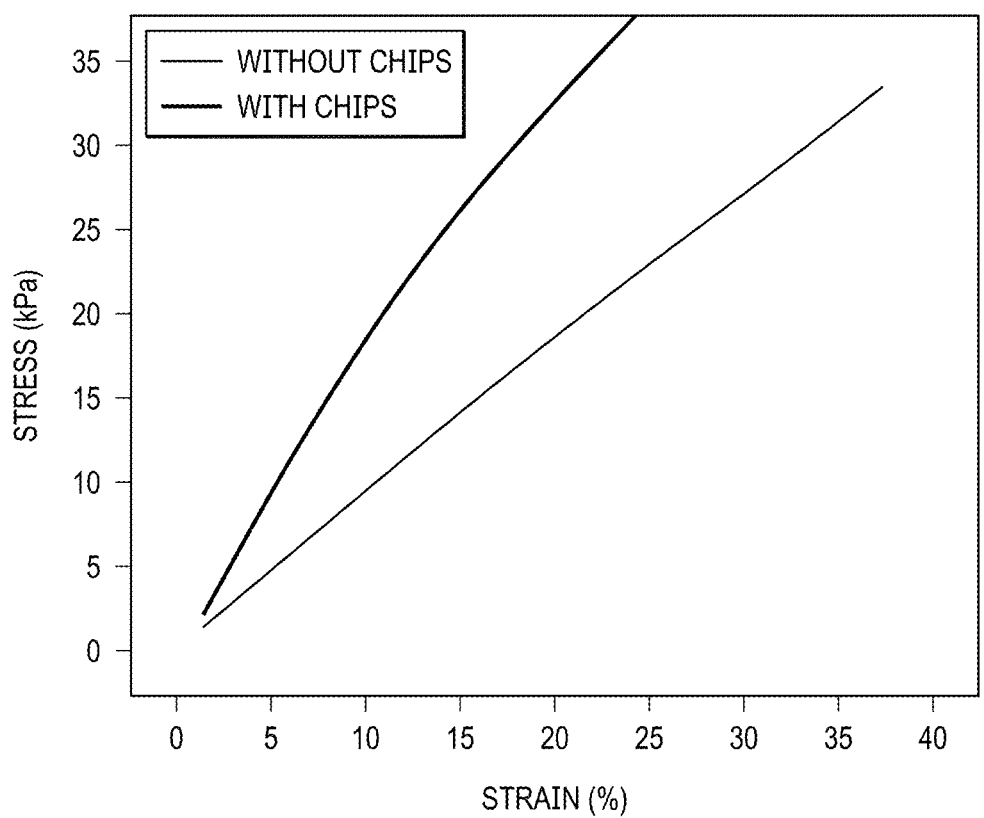
FIG. 9 is a plot illustrating the dynamic mechanical analysis of the device used in some embodiments with and without commercial chips bonded.
Figure 10A:
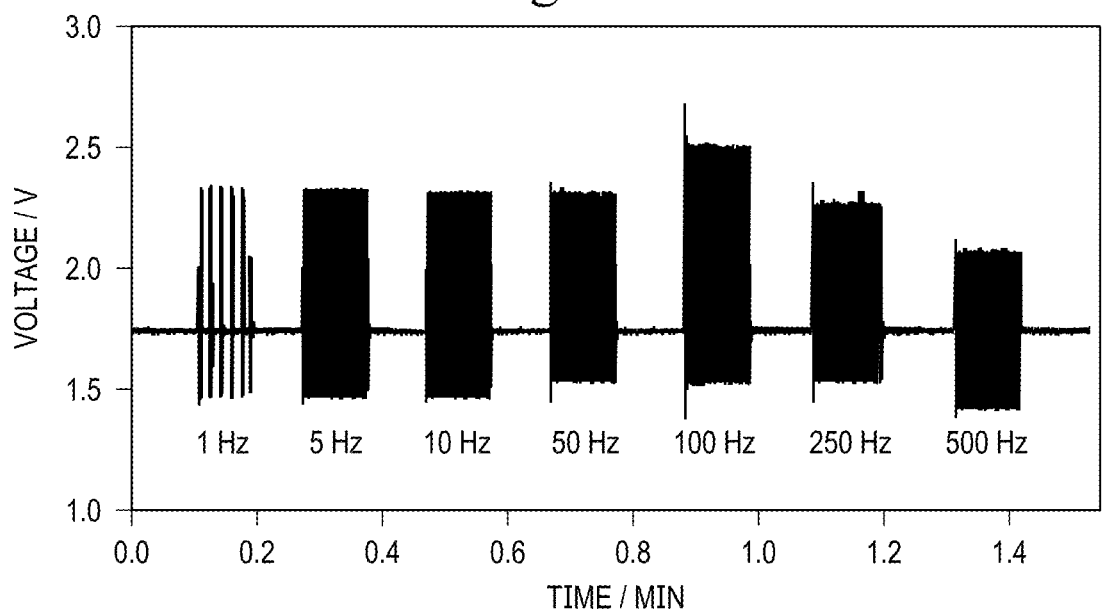
Figure 10F:
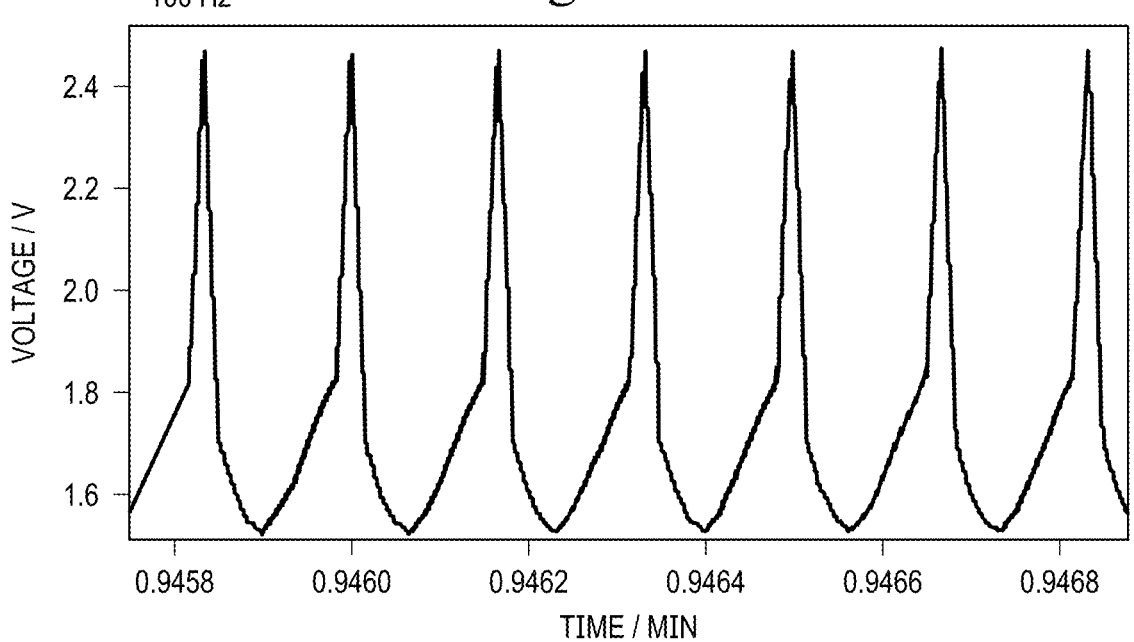
Figure 10G:
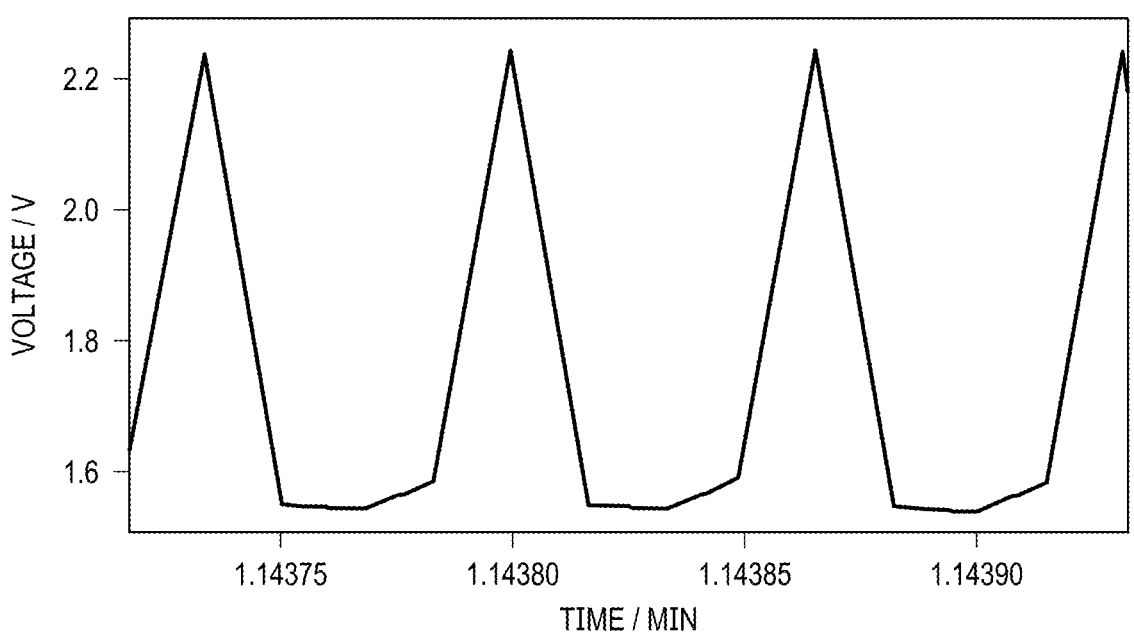
Figure 10H:
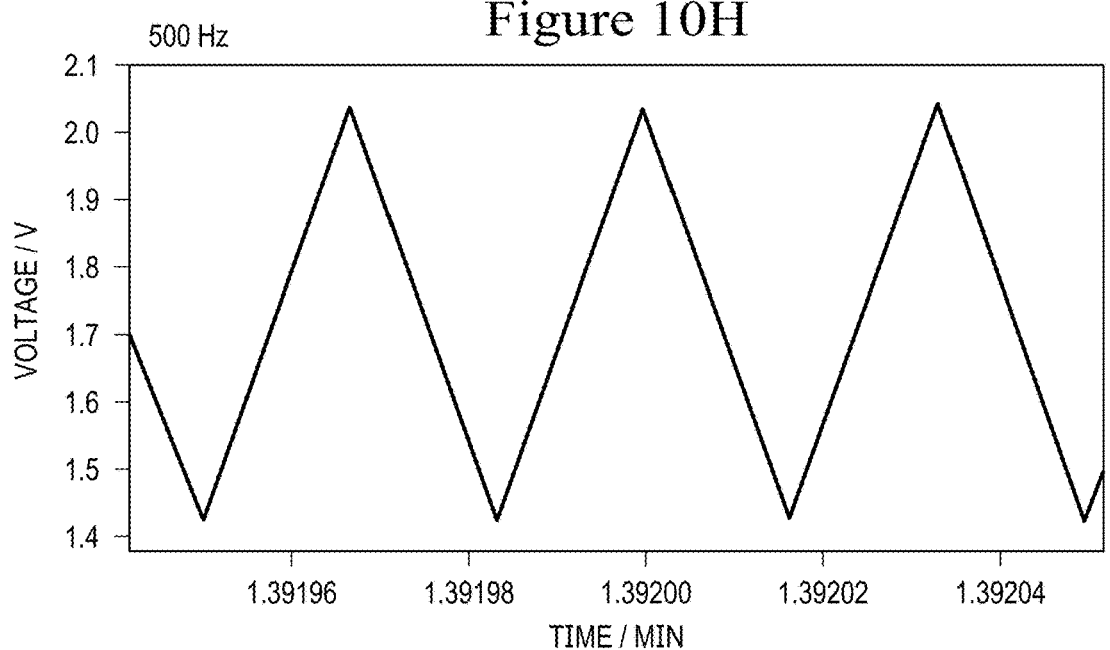

These strains can be reduced by increasing the interconnect lengths or the thickness of the core encapsulation material. FIG. 7B shows a magnified view of this region, where the influence of two adjacent components leads to a local region of strain concentration. The calculated strains are lower than the fracture strain of copper (~5%), indicating a total biaxial stretchability of the device that is larger than 25%. Stretching is mainly absorbed by deformations of the serpentine interconnects. Assuming a yield strain of ~0.3% in the copper, the elastic stretchability in both directions is ~4.6%. Results of 3D-FEA for an otherwise identical system, but without any of the device components, appear in FIGS. 8A-8B. The deformation patterns also show good agreement with experiment when biaxially stretched by 25%, with a similar strain concentration effect observed in the same region. Stress-strain measurements along the device length (FIG. 9) reveal effective moduli of ~32.1 kPa (with chips) and ~8.68 kPa (without chips), which are much smaller than those of the epidermis (~100 to 200 kPa), and confirm the stretchability of up to 25% strain. The layouts can be adjusted to meet application requirements.

Figure 11:
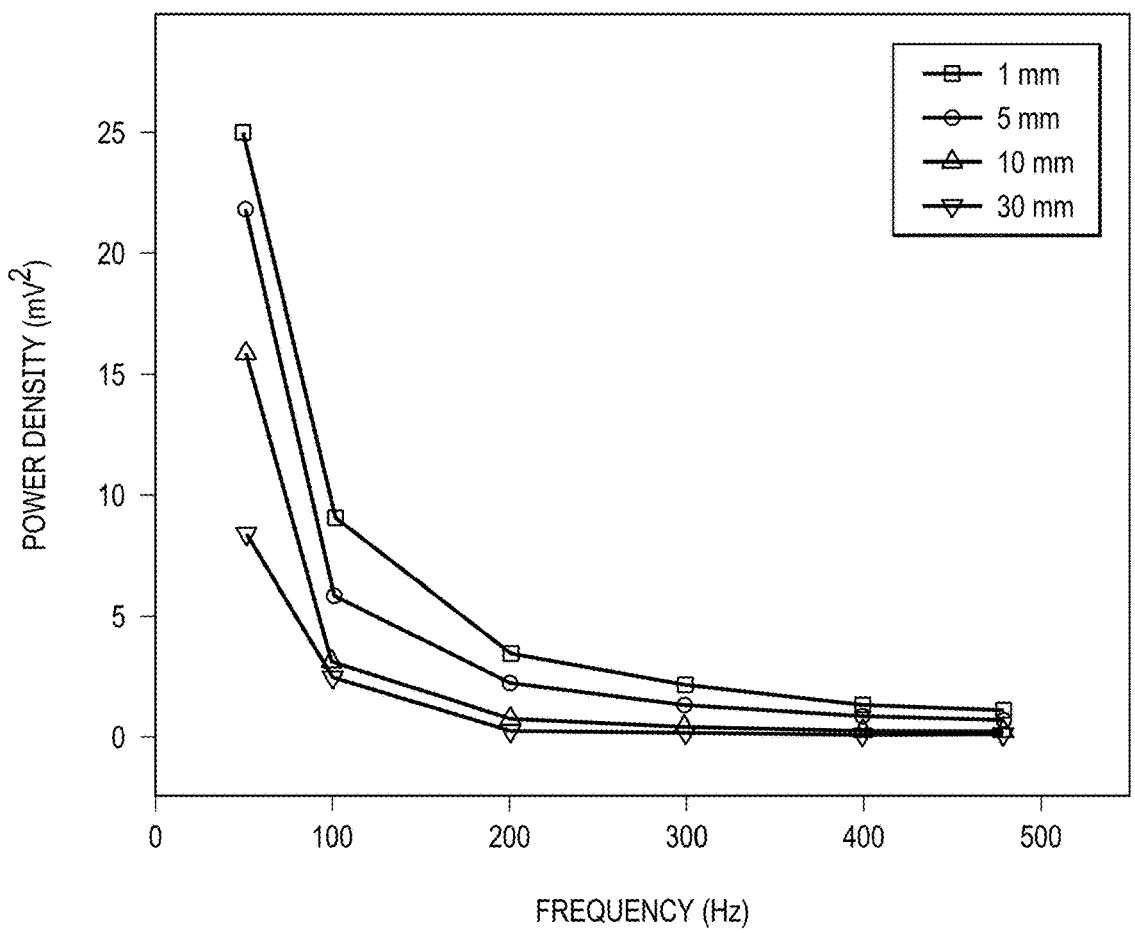
FIG. 11 is a plot of spectral power measured while mounted on a layer of chicken breast, to simulate tissue, on a vibration source.

The mechano-acoustic response captured without analog filters using a vibration simulator (e.g., 3B Scientific) shows the expected frequency bandwidth (FIGS. 10A-10H). For use on the body, the depth of the source varies according to the location and the associated organ. As examples, the larynx is ~5 mm below the surface of the neck, and the valves of the heart are ~30 mm away from the surface of the chest. In vitro experiments use fresh pieces of chicken breast, with thicknesses between 1 and 30 mm, placed between the sensor and the vibration simulator to simulate the effects of viscoelastic losses. Results indicate that the spectral power of the measured response exhibits a power law behavior with respect to signal frequency and an asymptotic decay with respect to tissue thickness (FIG. 11), as expected from the acoustic attenuation by absorption and scattering in viscoelastic materials and at the materials interfaces. The average decrease in spectral power between frequencies in the measurement range is 51% on 1-mm-thick tissue and 83% on 30-mm-thick tissue.

Partly because of this attenuation and partly because of the small amplitudes at the biological source, mechano-acoustic signals at the surface of the skin are relatively weak, and increasingly so with increasing frequency. Therefore, measurements must account for effects in mechanical loading and mechanical impedance matching between the devices and the skin. The mass of the sensor system is an important characteristic in this regard. Increasing the device mass increases the mechanical loading at the skin interface, thereby decreasing the mechano-acoustic motions. In vitro experiments to demonstrate these effects involve experiments such as those described above but with the sensor placed in an acrylic box (19 mm×42.5 mm×55 mm, 9.36 g) with different added test masses (FIG. 12).

Figure 12A:
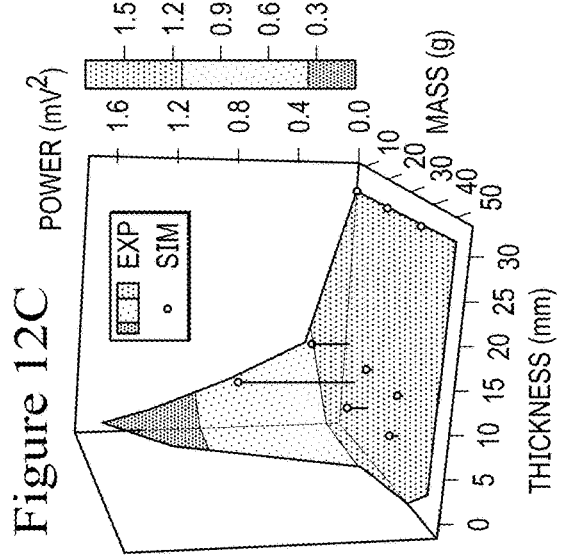
FIGS. 12A-12C illustrate experimentally measured spectral power and simulation results associated with the mechano-acoustic response of a device mounted in an acrylic box placed on a tissue sample on a vibrational source at frequencies of 50 Hz (A), 100 Hz (B), and 200 Hz (C)
Figure 12B:
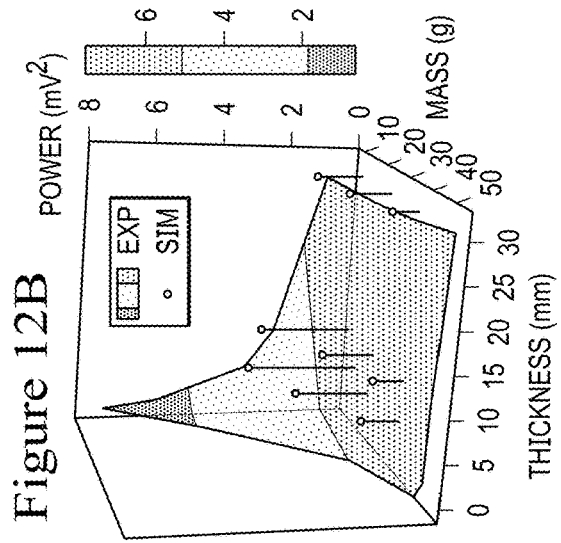
Figure 12C:
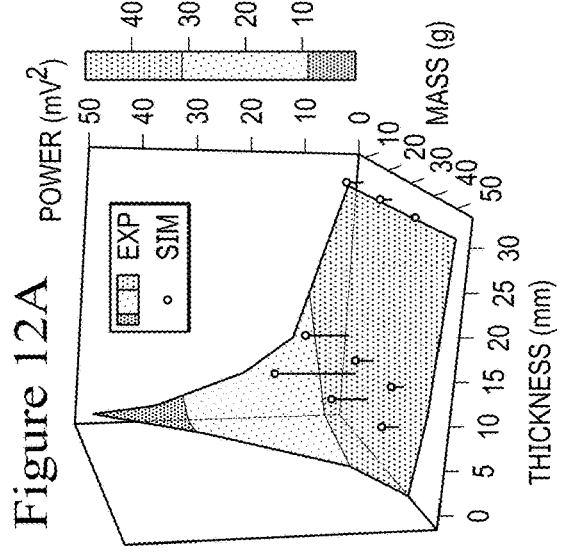
Figure 12D:
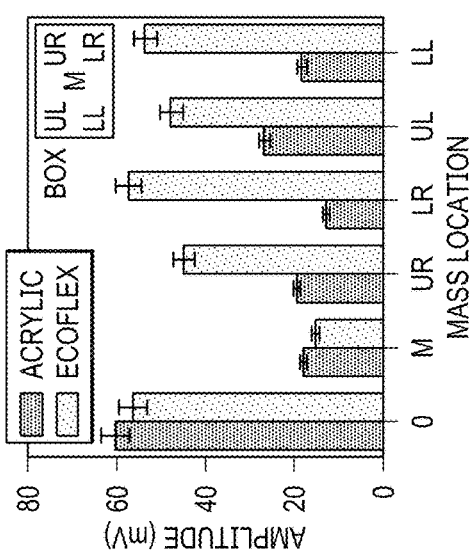
FIG. 12D is a comparison of measured (experiment) and computed (analytical) dependence of spectral power on mass.
Figure 12E:
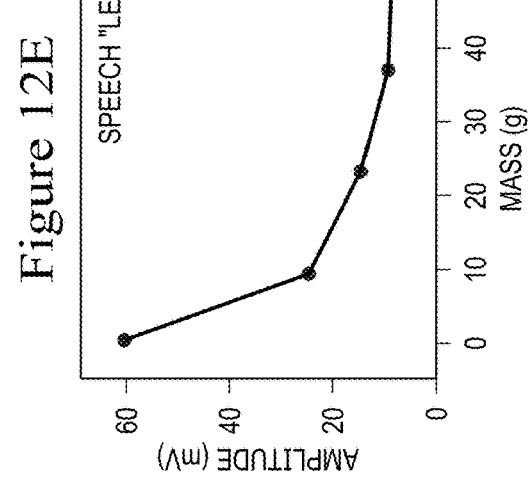
FIG. 12E is a measured maximum signal amplitude recorded with a device mounted on the neck as the subject said the word "left," as a function of the mass of the device.
Figure 12F:
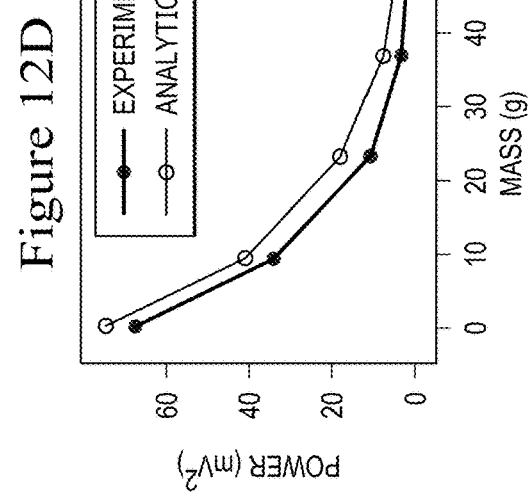
FIG. 12F Amplitude measured using a device in a rigid box and on a thin substrate of Ecoflex, as a function of spatial location of the added mass.

Results in FIGS. 12A-12C show a general trend of decreasing spectral power with tissue thickness and mass for all frequencies within the accelerometer bandwidth. The additional mass in this case has negligible effect. A simple mechanical model consisting of a mass, a spring, and a damping source can capture the overall behaviors (FIG. 12D). The computed results at three different frequencies (50, 100, and 200 Hz) indicate that the response decreases with increasing mass, tissue thickness, and frequency. In vivo studies of speech recognition confirm that increasing mass leads to decreasing signal (FIG. 12E).

In addition to overall device mass, the distribution of this mass and the overall mechanics of the structure are important. In particular, in a soft, low-modulus device platform, only the mass of the mechano-acoustic sensor chip is important, whereas in a rigid platform, the overall mass limits the performance. Results in FIG. 12F verify that in a low-modulus device platform, added mass is only significant when located at the position of the sensor, and that added mass at different locations has similar loading effects for the case of a rigid platform. FEA of a similar system is consistent with the experimental data. These findings suggest that low-mass and low-modulus characteristics are critically important. An additional implication is that, in the physical forms reported here, batteries, radios, and other components of interest for future embodiments can be included in the platform without adversely affecting the measurement sensitivity.

Seismocardiography Measurement

Figure 13A:
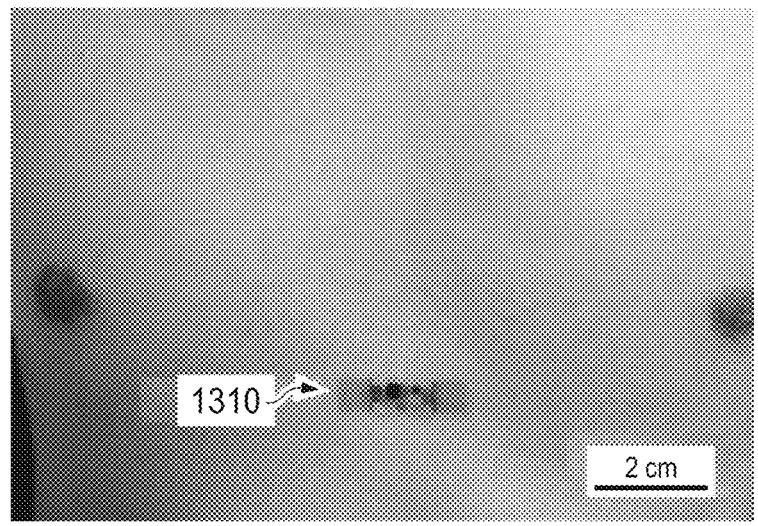
FIG. 13A shows an image of an epidermal device mounted on the chest.

Seismocardiography (SCG) captures the thoracic vibrations from atroventricular contractions and blood ejection into the vascular tree on the skin of the sternum. Each beat cycle produces a characteristic SCG complex as a quasi-periodic waveform with frequency components that reflect contraction of the heart muscle and associated ejection of blood. FIG. 13A shows the mechano-acoustic device 1310 and its pair of conformal capacitive electrodes laminated onto the sternum for simultaneous measurements of SCG and ECG.

Figure 13B:
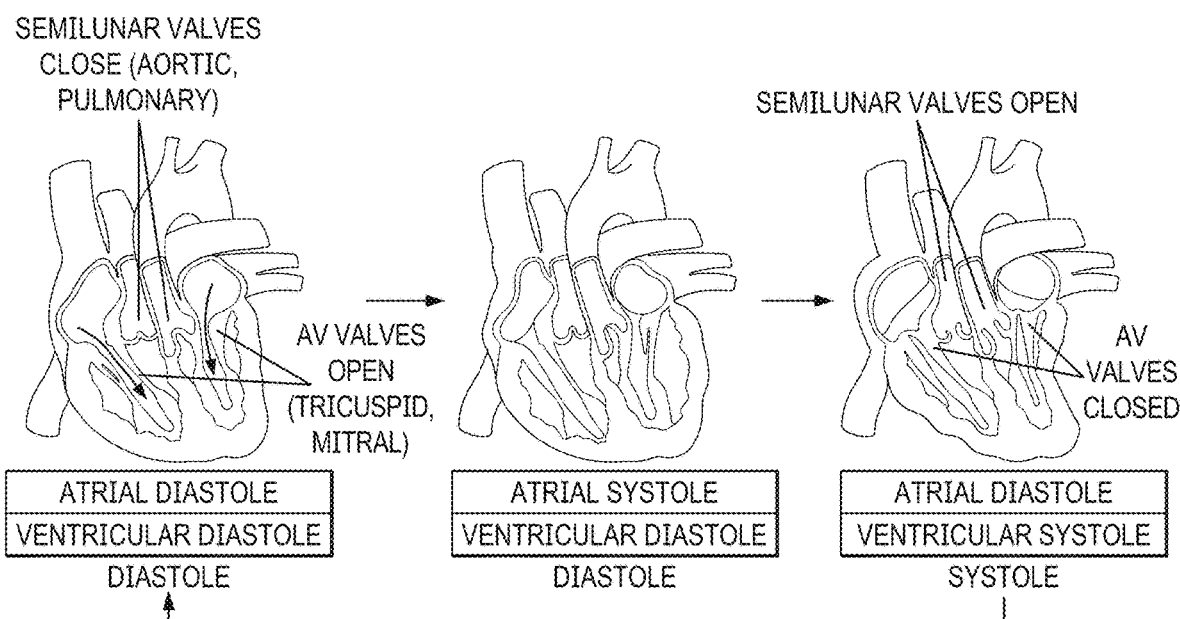
FIG. 13B is a schematic diagram of cardiac cycle: (left) artrial and ventricular diastole, (middle) artrial systole and ventricular diastole, and (right) ventricular systole and atrial diastole.
Figure 13C:
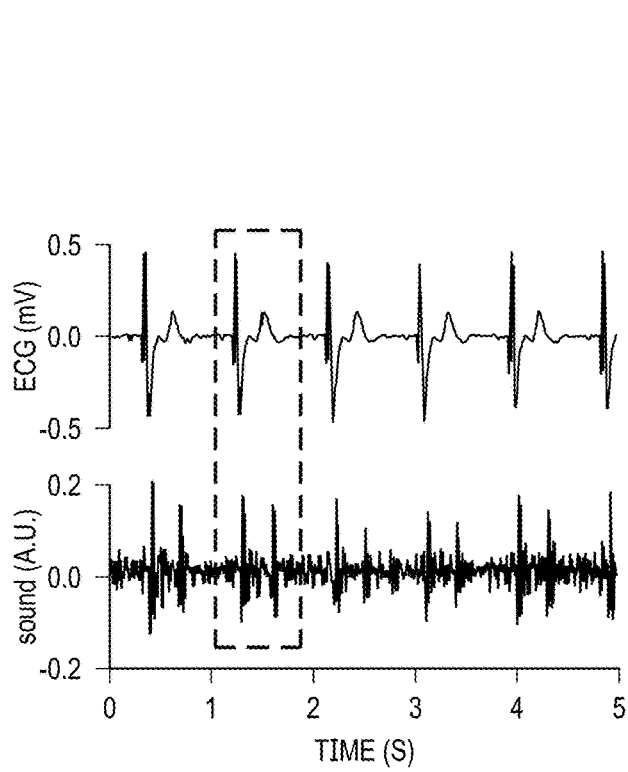
FIG. 13C is a plot of ECG (top) and heart sound (bottom) signals measured simultaneously. A.U., arbitrary units.
Figure 13D:
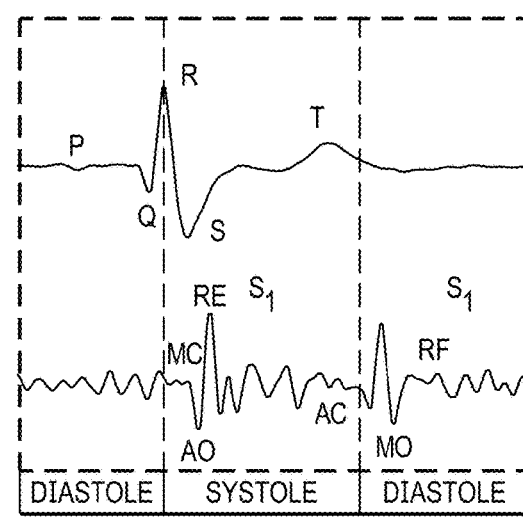
FIG. 13D is a magnified view of ECG (top) and heart sound (bottom) signals measured in FIG. 13C.

A single cardiac cycle includes systole (contraction of heart muscle) and diastole (relaxation of heart muscle) motions of the atria and the ventricles, as illustrated in FIG. 13B. These motions involve electrical signals followed by mechanical coupling and a sequence of mechano-acoustic signatures as the heart chambers contract and the valves close. These electrophysiological and mechanical data form the basis of ECGs and cardiac auscultations, respectively. FIG. 13C shows ECG and SCG signals measured simultaneously from a healthy male subject (age, 22). Magnified views of a single cardiac cycle (FIG. 13D) highlight all the key features of these two waveforms. This information is useful in the assessment of systolic and diastolic ventricular function. For example, the electromechanical activation time (the time interval from the onset of the QRS to the point of peak intensity of S1) corresponds to the time required for the left ventricle (LV) to achieve sufficient pressure to force the mitral valve to close. Its prolongation indicates systolic heart failure. Reductions in the interval between S1 and S2 (termed left ventricular systolic time) are a sign of LV dysfunction. Overall, the data from the epidermal mechano-acoustic sensors reported here have a quality comparable to that of the data obtained using a commercial electronic stethoscope (e.g., JABES Electronic Stethoscope, GS Technology Co.), where S1 and S2 are delineated (FIG. 12E). This device can also measure pressure pulse waves associated with arterial blood flow. A sensor 1410 placed on the carotid artery at the neck (FIG. 14A) can capture these data, along with ECG signals (FIGS. 14B-14C).

Figure 13E:
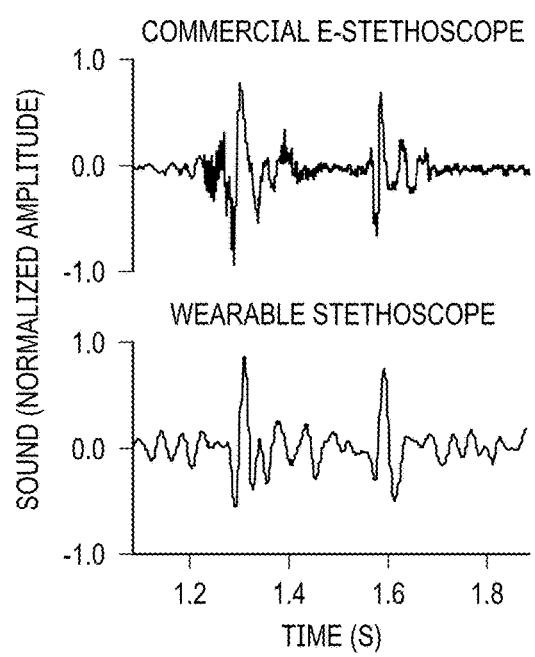
FIG. 13E is a comparison of heart sound signals measured using a commercial electronic stethoscope and the reported device.
Figure 13F:
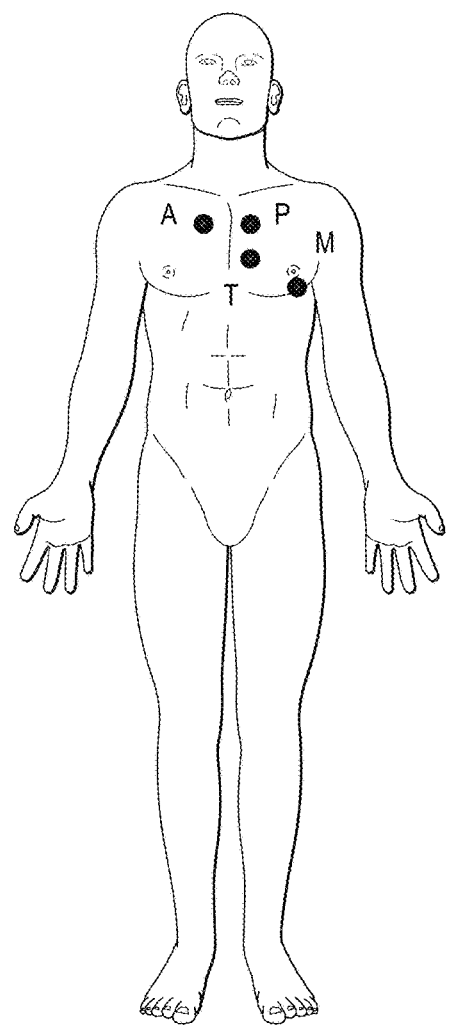
FIG. 13F is a schematic illustration of the measurement site: A, aortic; P, pulmonary; T, tricuspid; M, mitral.
Figure 13H:
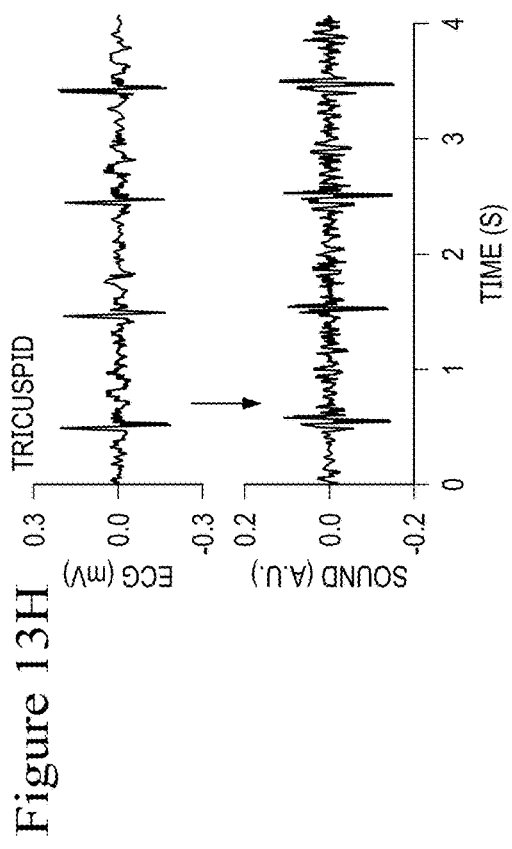
FIGS. 13G-13J show representative measurements from a 78-year-old female patient with diagnosed mild pulmonary and tricuspid regurgitation at the aortic (G), tricuspid (H), pulmonary (I), and mitral (J) sites.
Figure 13G:
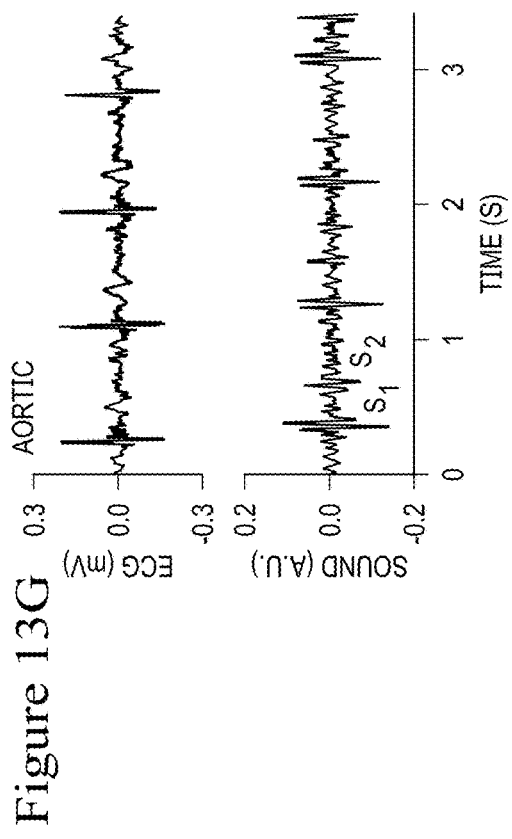
Figure 13J:
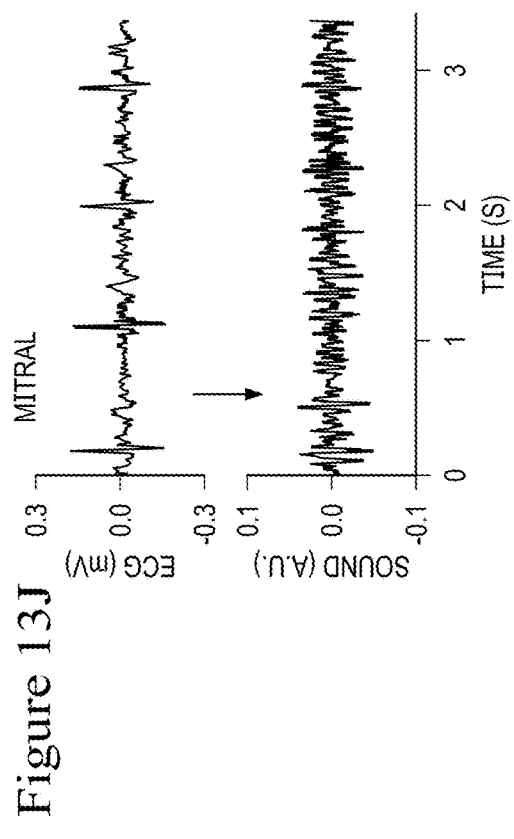
Figure 13I:
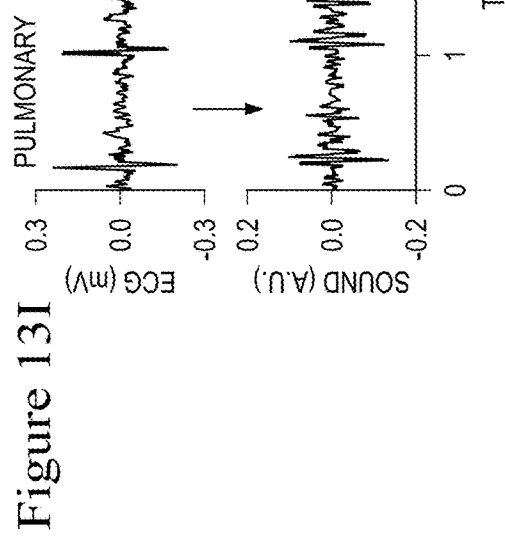

For subjects with cardiovascular pathologies, murmurs are often present in addition to signatures associated with S1 and S2. The holosystolic murmurs of the mitral and tricuspid valve regurgitation that occur during systole have acoustic signatures of characteristic constant intensity and high frequency. In contrast, diastolic murmurs are often detected in patients with aortic or pulmonic valve regurgitation. Clinical validation of the device operation in this context involves recording cardiac mechano-acoustic responses with ECG signals from eight patient volunteers diagnosed with cardiac valvular stenosis or regurgitation. FIG. 13E is a comparison of heart sound signals measured using a commercial electronic stethoscope and the device according to some embodiments of the present technology. FIG. 13F is a schematic illustration of the measurement site: A, aortic; P, pulmonary; T, tricuspid; and M, mitral. FIG. 13G shows the auscultation mounting sites that yield optimal results for the aortic, pulmonary, tricuspid, and mitral heart valves.

Figure 15A:
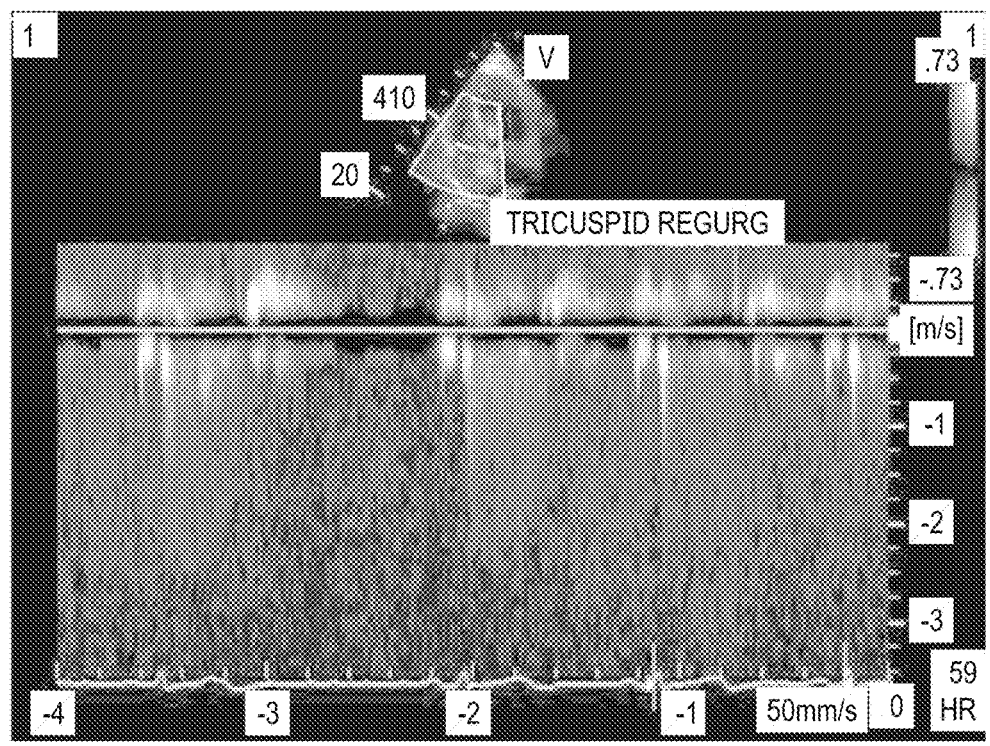
FIGS. 15A-15B illustrate echocardiogram characterization results on a patient with tricuspid and pulmonary regurgitation with FIG. 15A illustrating the chocardiography in the top and ECG at the bottom for tricuspid valve measurement, and FIG. B the pulmonary valve measurement.
Figure 15B:
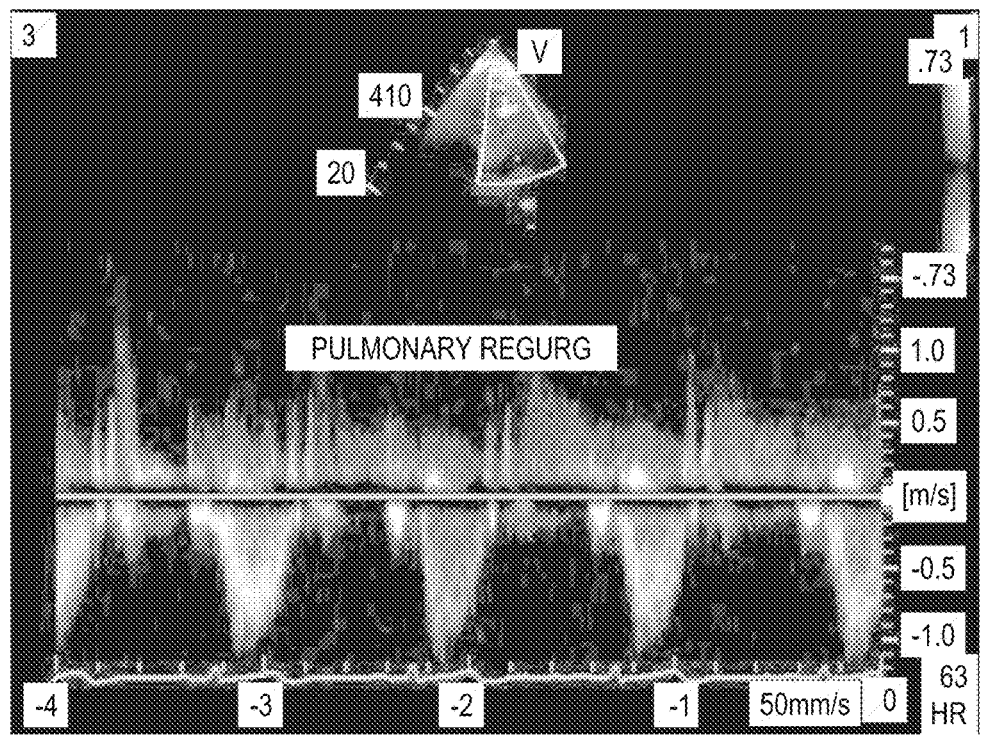
Figure 16A:
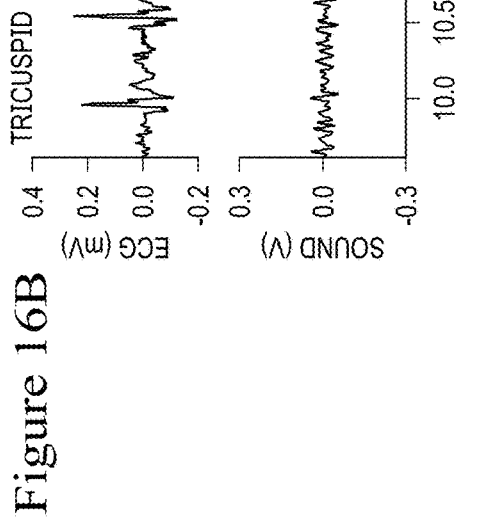
FIGS. 16A-16D illustrate a representative measurement from an 82 year-old female patient with diagnosed mitral and tricuspid regurgitation at aortic site (FIG. 16A), tricuspid site (FIG. 16B), pulmonary site (FIG. 16C), and mitral site (FIG. 16D)
Figure 16B:
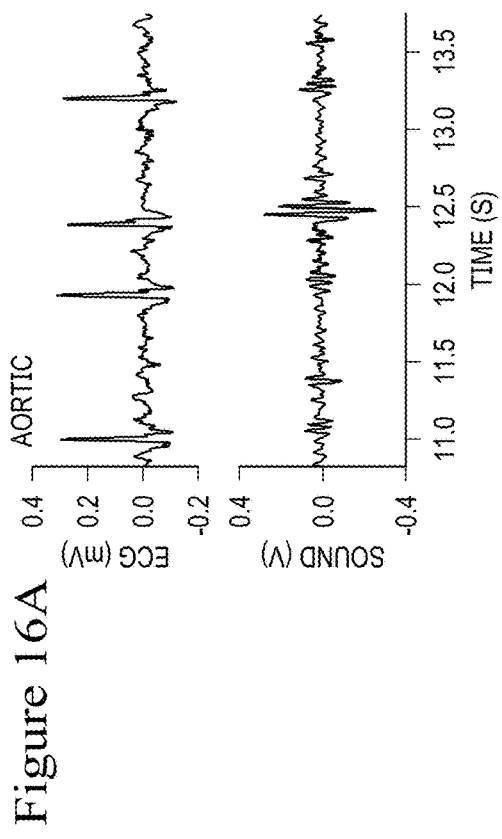
Figure 16C:
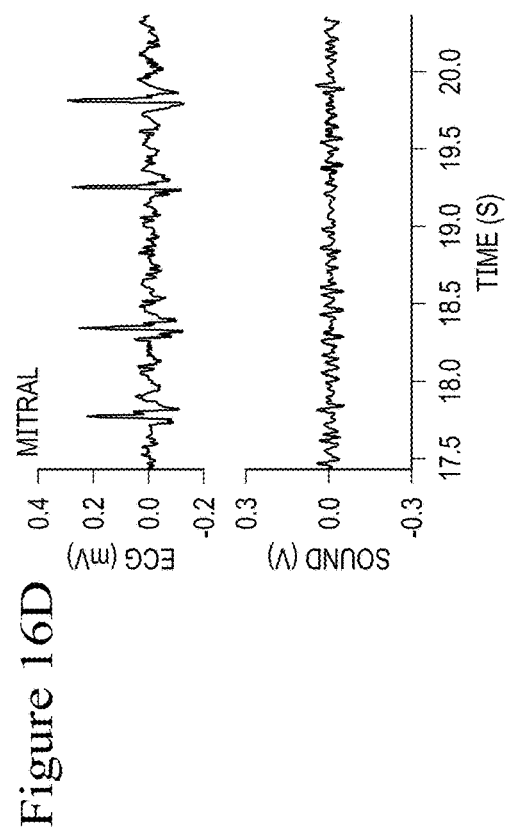
Figure 16D:
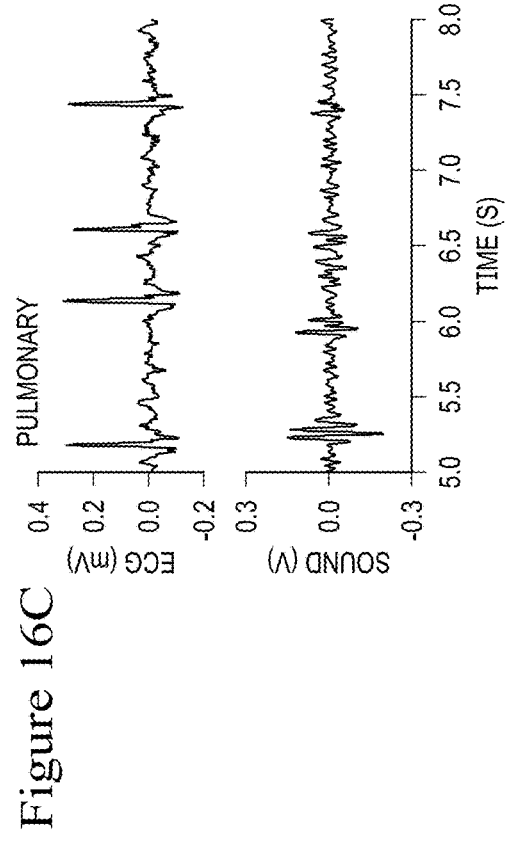

An elderly female patient (age, 78) with diagnosed mild tricuspid and pulmonary regurgitation via echocardiography (FIGS. 15A-15B) manifests a short, constant intensity murmur at tricuspid and pulmonary sites in systole and diastole, respectively, as indicated by the arrows in FIGS. 13G-13J. Measurement from the aortic site shows no signs of stenosis or regurgitation. Signal from the mitral site is weak, likely because of nonoptimal sensor placement. FIGS. 16A-16D show a female patient (age, 82) with severe regurgitation of the tricuspid and mitral valve and an irregular beat rate. Studies on other related patients yield similar data.

Acoustic Analysis of VAD

Additional biomedical applications include monitoring of mechanical circulatory support devices, such as those that augment dysfunctional ventricular pump function and serve as important temporary or permanent alternatives to heart transplantation. The latest continuous flow left ventricular assist devices (LVADs) offer improved durability and hemodynamic restoration, though with the limitation of adverse events, including a loss of pump function due to pump thrombosis or other mechanical failure. Previous work in the context of the first failure mode shows that the formation of blood clots on the rotor leads to changes in the sounds of the pump. These changes can be difficult or impossible to discern using stethoscopes or unaided human hearing, particularly for early-stage thrombosis. Various embodiments of the mechano-acoustic sensors enable a surface-mounted mode to monitor changes in vibration signatures in the LVAD pump. Studies discussed below focus on an in vitromodel with a commercial LVAD (e.g., HeartMate II, Thoratec Corporation) and continuous flow to detect changes in acoustic signal correlating to variation in pump speed, circulating fluid, and thrombus embolization.

Figure 17A:
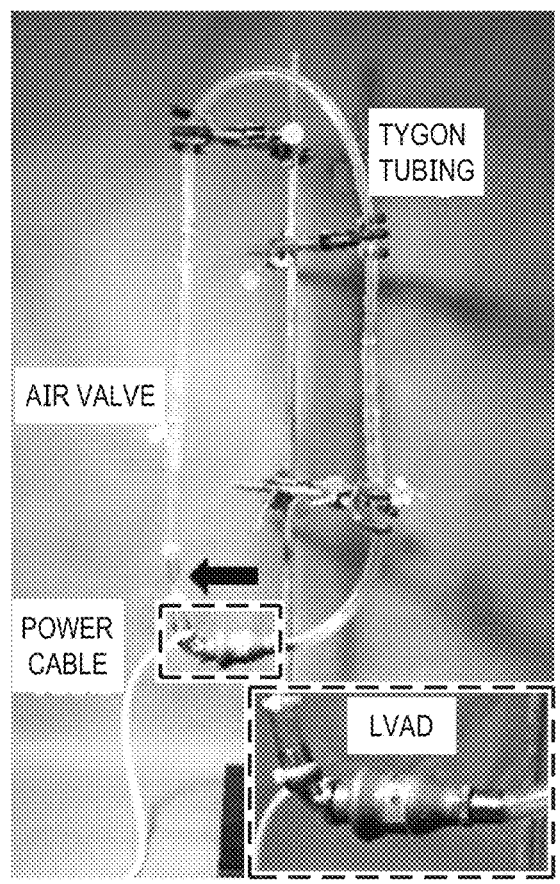
FIGS. 17A-17B show an experiment on LVAD pump thrombosis with FIG. 17A showing an image of a HM II LVAD device and FIG. 17B showing an image of a 500 μL blood clot injected into the circulation loop.
Figure 17B:
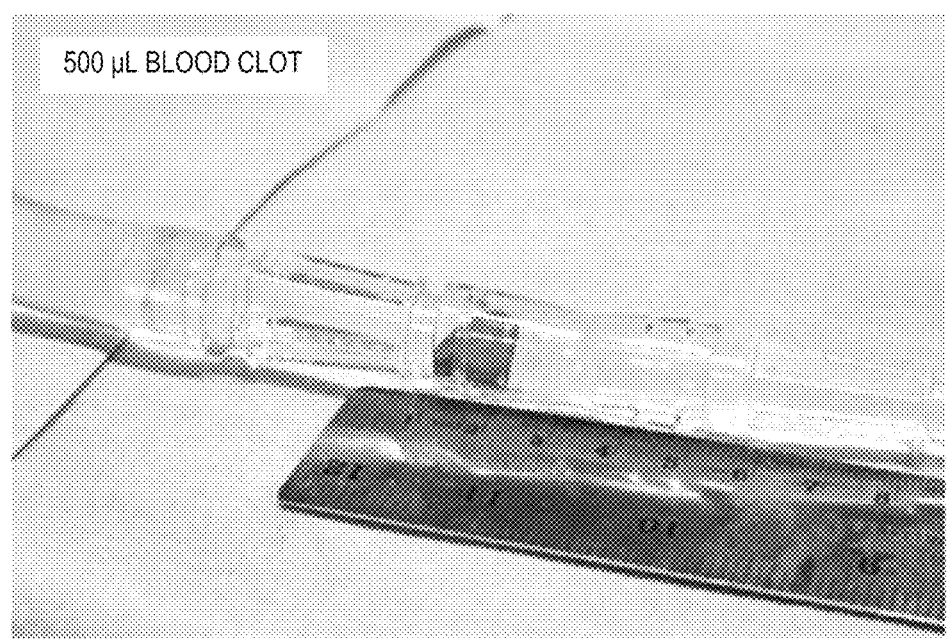
Figure 18C:
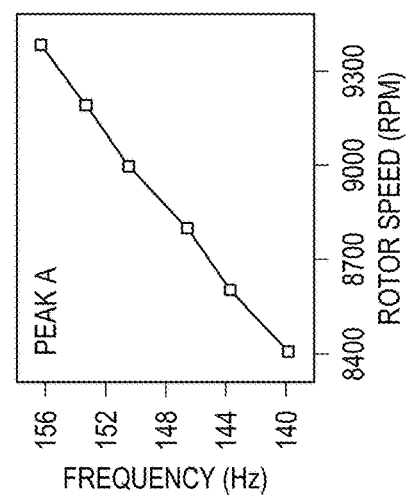
FIG. 18C shows the FFT spectral power of the vibration response for operating frequencies between 8400 and 9400 rpm (not the distinctive changes with VAD speed occur only on the peak around 150 Hz)
Figure 18B:
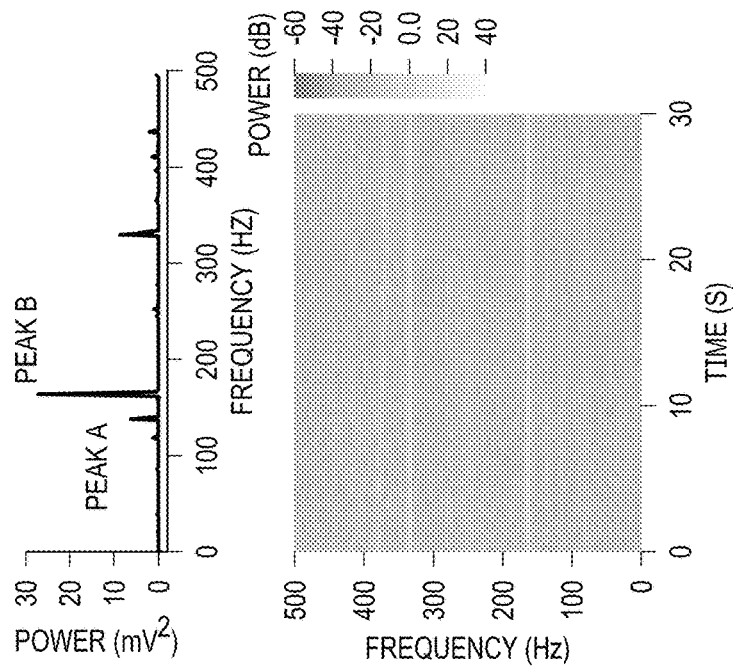
FIG. 18B shows a Fast Fourier transform (FFT) of the vibration response (top) and spectrogram (bottom) associated with the operation of the VAD at 8400 rpm in a water circulation loop.
Figure 18A:
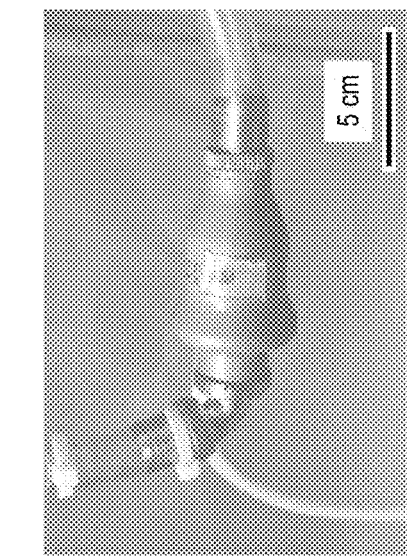
FIG. 18A shows an image of the experimental circulation loop with the device mounted on the VAD (HeartMate II)

FIGS. 17A-17B show a system consisting of a circulatory closed loop that involves medical grade tubing (e.g., Tygon) connected to HeartMate II, with valves to assist in the removal of air bubbles and to allow the introduction of blood clots. The device laminates conformally onto the metal housing of the pump impeller and brushless dc motor to provide direct measurements of vibration (FIG. 18A). The spectral power of the signal collected for a short time (e.g., 30 s) during operation of HeartMate II at 8400 rpm appears in FIG. 18B. The bottom panel in FIG. 18B shows characteristic signatures at 139.7 Hz (peak A) and 166 Hz (peak B) and its second harmonic at 332 Hz. Increasing the pump speed from 8400 to 9400 rpm leads to decreases in the frequency of peak A from 139.7 to 156.2 Hz (FIG. 18C), whereas peak B remains unchanged (FIG. 18D).

These data suggest that peak A can serve as a reliable indication of the pump speed. Replacing water with glycerol, a fluid medium with a viscosity similar to that of blood serumbut higher than that of water, leads to no significant change in the acoustic signature (FIG. 18E). This result suggests that the pump rotation dominates collected acoustic signatures, and that they are insensitive to changes in circulating fluid viscosity.

Introducing a blood clot (500 µL) (FIG. 17B) prepared from bovine whole blood through the air valve at the inflow of the HeartMate II during glycerol operation at 9400 rpm serves to simulate thrombosis and embolization. Immediately after injection, the blood clot travels through the LVAD and exits the outflow tubing with minimal distortion. The associated widening of peak A suggests that clot interaction with the pump impeller produces additional frequencies (FIG. 18F, top panel). While the clot travels through the remainder of the circulation loop, the pump remains undisturbed, and the vibration signature returns to its initial, that is, two-peak state, but with peak A at a higher amplitude than peak B (FIG. 18F, second panel), possibly as a result of tiny blood clots attached to the pump impeller.

After several passages, the clot dissipates completely into microscopic fragments invisible to the unaided eye. This process creates another strong group of frequencies around peak A (FIG. 18F, third panel). Finally, the vibration signature restores to the circulation state, with peak A again at higher amplitude, confirming previous observation (FIG. 18F, bottom panel). These results serve as a reference that validates the possible use of an accelerometer to capture acoustic signatures in the LVAD for pump thrombosis detection and monitoring.

Speech Recognition and Human-Machine Interface

Figure 19A:
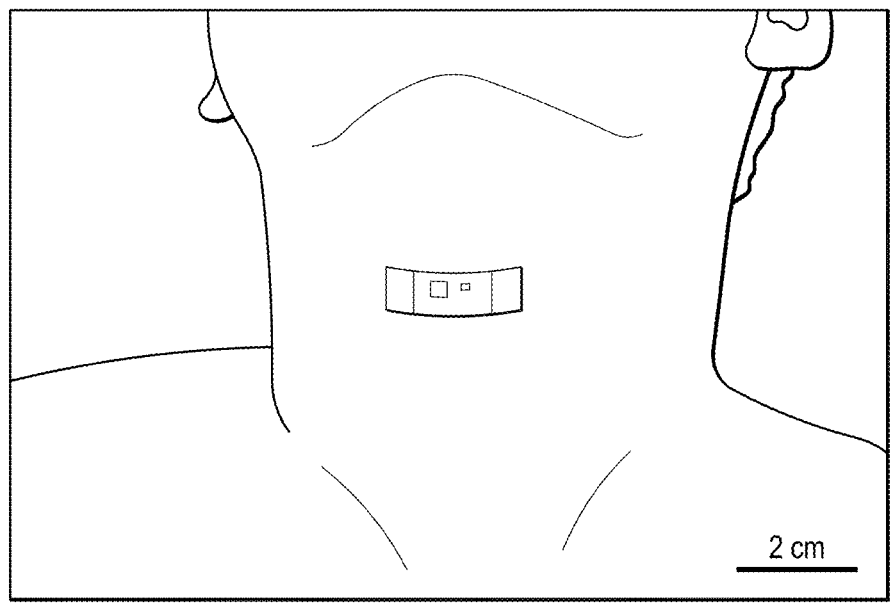
FIG. 19A is an image of an epidermal device mounted on the vocal cords.

Two features of epidermal mechano-acoustic devices (FIG. 19A), specifically their use of multiple sensors in a single device platform and their compatibility with direct placement on curvilinear regions of the skin, enable their application in speech capture and recognition. Implications range from improved communication capabilities for individuals with speech impairments to the design of voice-activated human-machine interfaces.

Figure 19B:
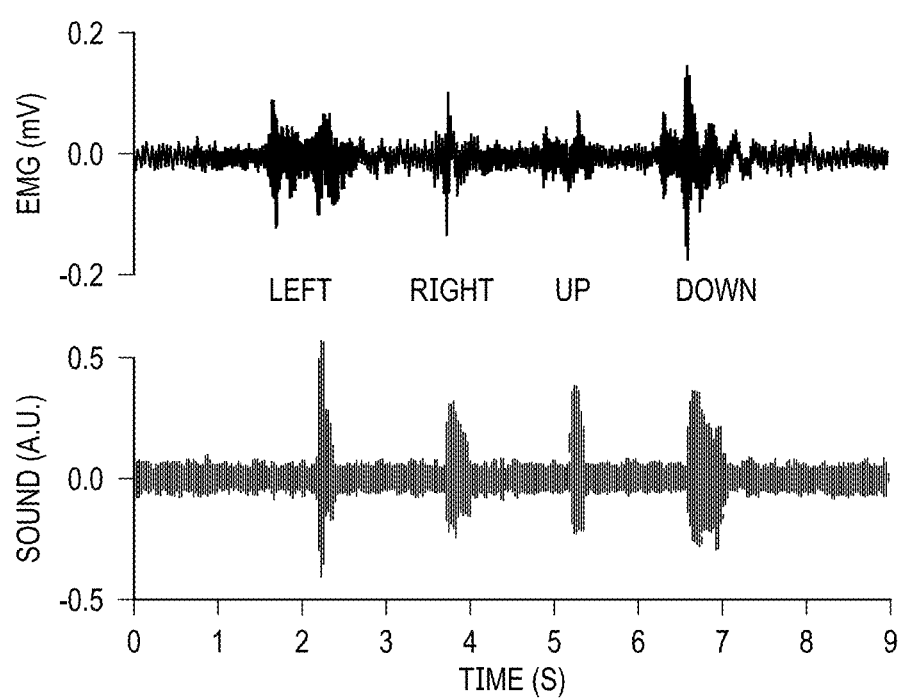
FIG. 19B is a plot of EMG (top) and vocal vibrational (bottom) signals measured simultaneously from the neck.

First, with appropriate placement, epidermal mechano-acoustic devices can simultaneously capture both electromyogram (EMG) signals from articulator muscle groups and acoustic vibrations from the vocal cords. FIG. 19B shows EMG signals (top) and mechano-acoustic vibrations (bottom) recorded while speaking "left," "right," "up," and "down." The spectrogram (FIG. 19C, top left) highlights the unique time-frequency characteristics of each of the four words. The low-frequency components of the nasal consonant in "down" are particularly prominent. Previous research suggests that the fusion of multiple sensors can improve speech recognition. A specific suggestion is that throat EMG can enhance traditional speech recognition techniques, although simultaneous recording of EMG and acoustics in a single device has not been demonstrated. An earlier study showed that fusion of acoustic data with EMG signals measured using separate devices improved word recognition accuracy in a small group of patients with dysarthria.

Figure 19C:
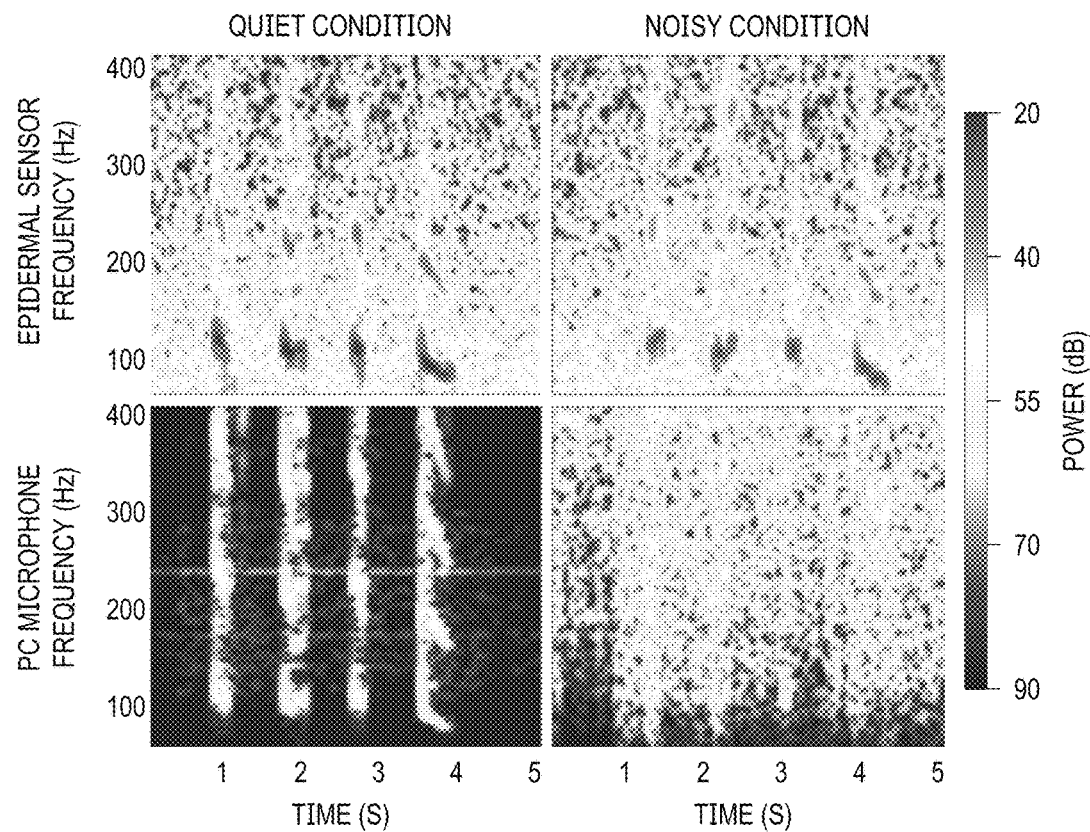
FIG. 19C illustrates a comparison of speech recorded with the reported device (top) and with an external microphone (bottom). The left and right columns represent recordings made under quiet and noisy conditions, respectively.
Figure 20:
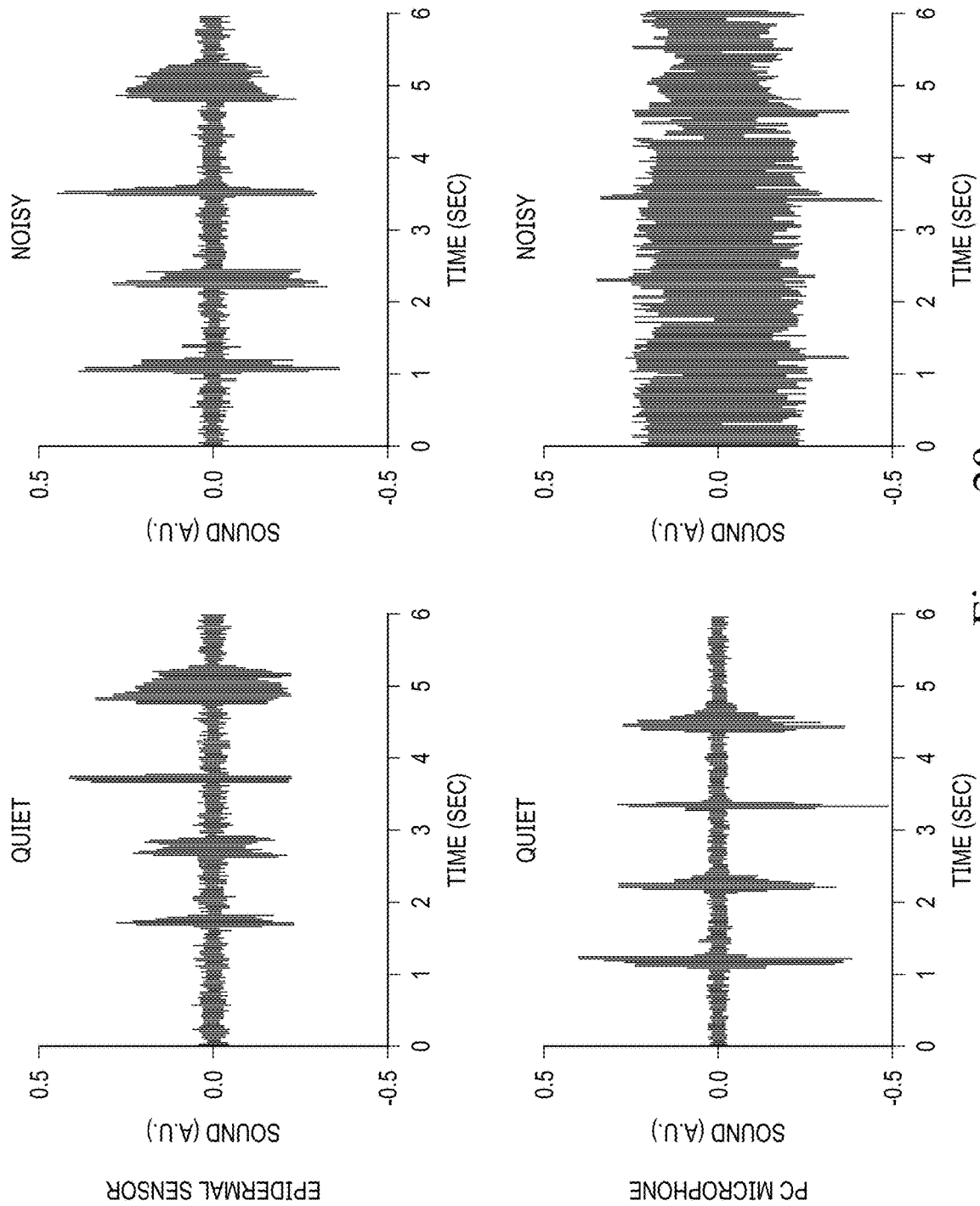
FIG. 20 illustrates data captured using a reported device and a commercial microphone in quiet and noisy environments.
Figure 22A:
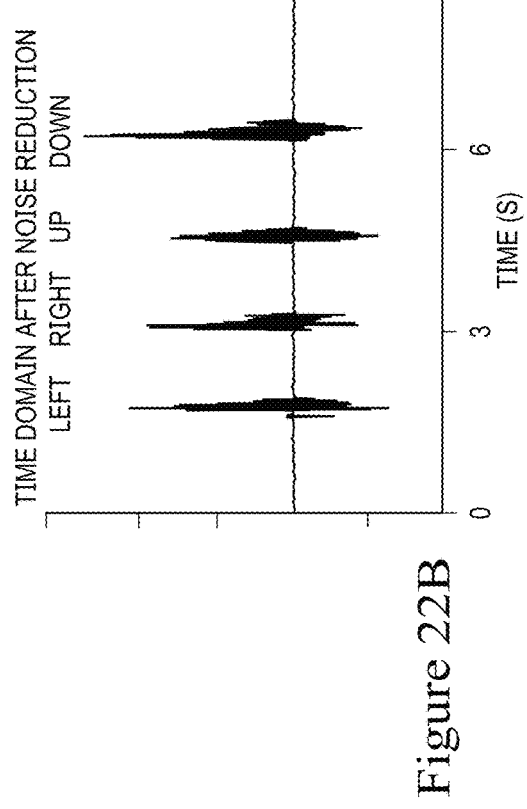
FIGS. 22A-22F illustrate a demonstration of noise reduction in time domain speech data.
Figure 22B:
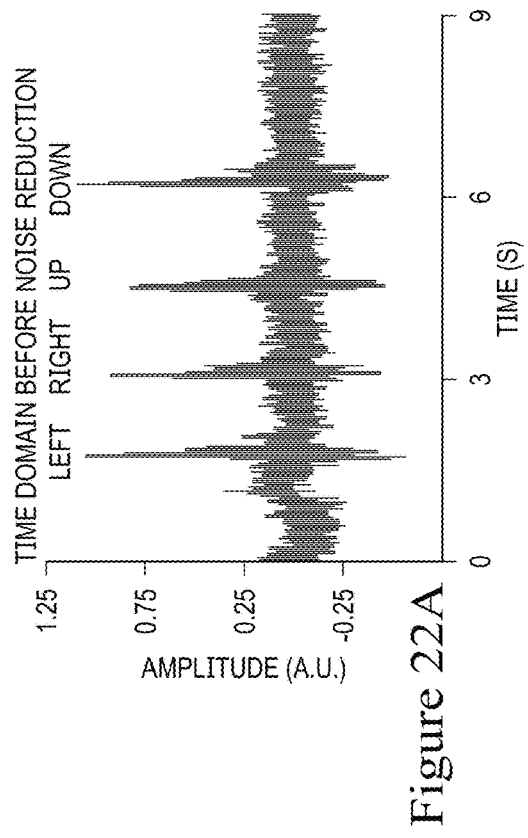
Figure 22C:
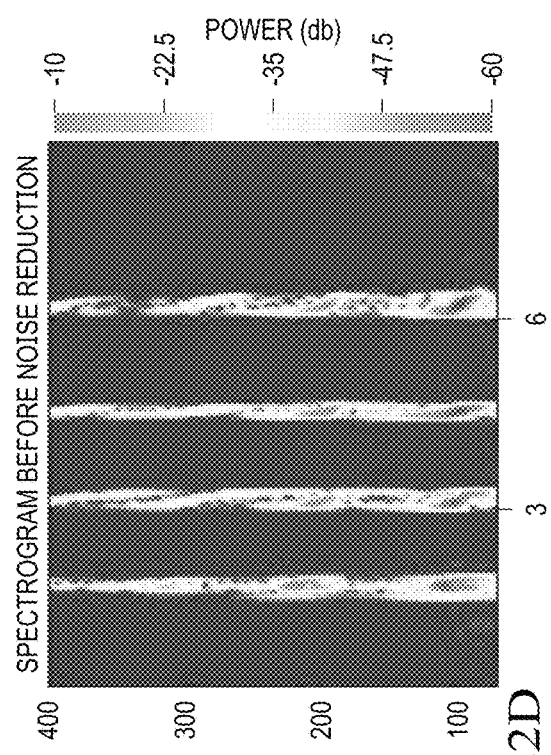
Figure 22D:
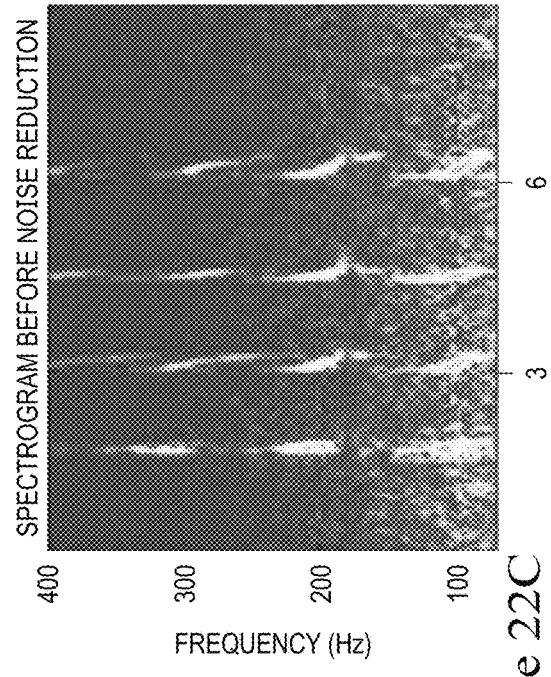
Figure 22E:
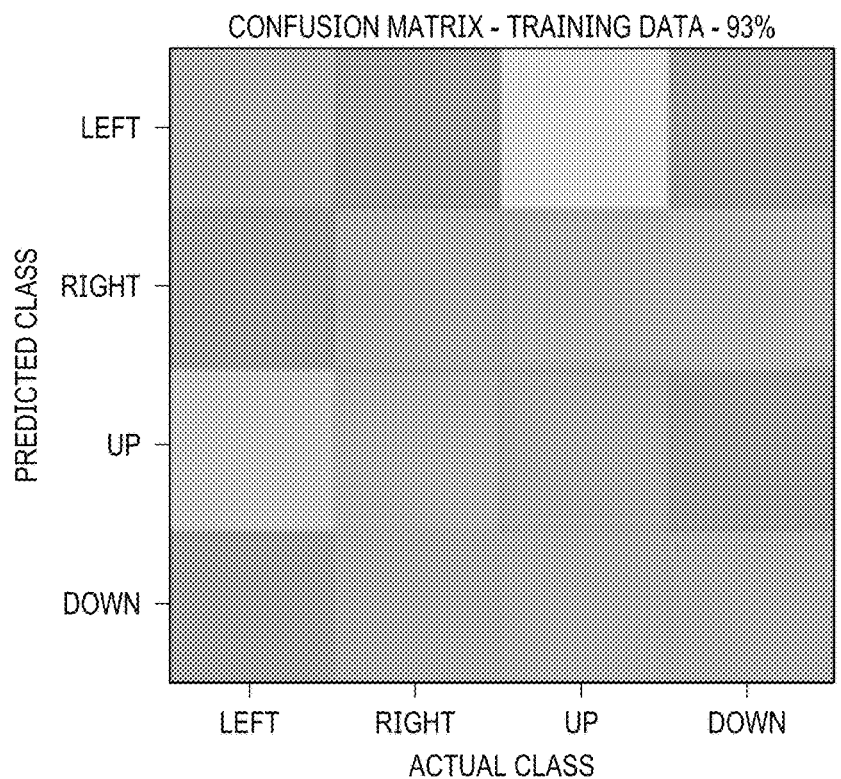
Figure 22F:
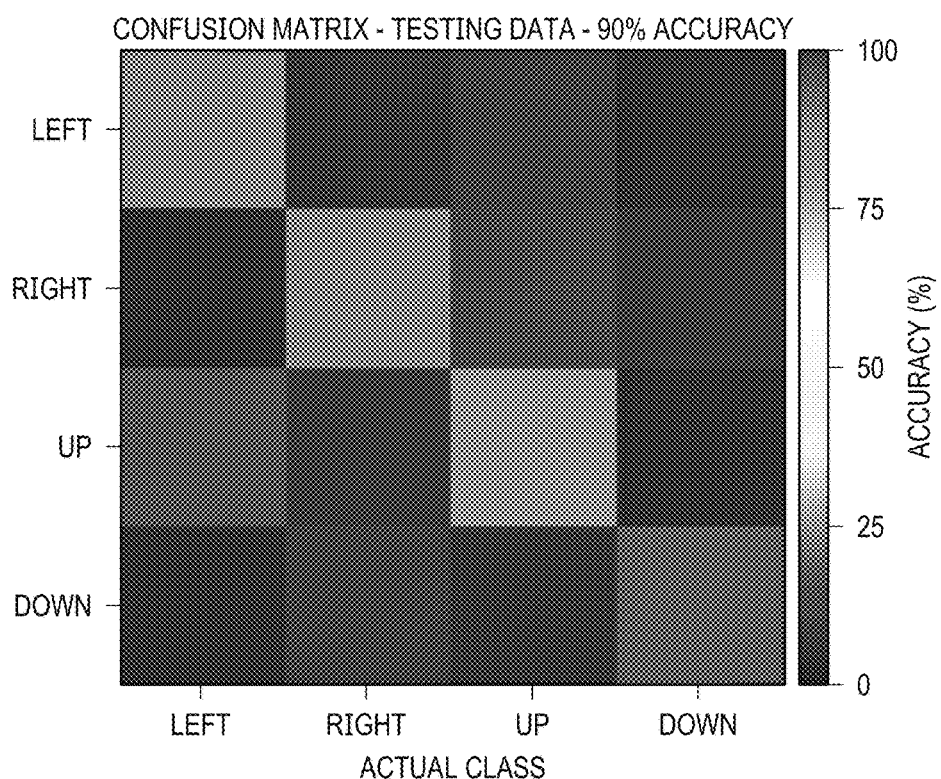

Second, the intimate contact between the sensors and the skin renders their operation almost unaffected by ambient acoustic noise. FIG. 19C compares spectrograms of speech ("left," "right," "up," and "down") recorded by an epidermal sensor and by a standard microphone (e.g., iPhone, Apple Inc.; see FIG. 20 for time domain data), both attached to a subject's throat. The noise source (e.g., radio speakers) is 2.5 m away from the subject. In a quiet environment (e.g., ~30 dB (62)), both the epidermal sensor and the microphone show similar responses. On the other hand, a noisy environment (e.g., ~60 dB (62)) significantly degrades the quality of recording from the microphone but does not affect the epidermal sensor. This feature could allow the epidermal acoustic sensor to be used for communication in loud environments by first responders, ground controllers, or security agents.

Figure 21:
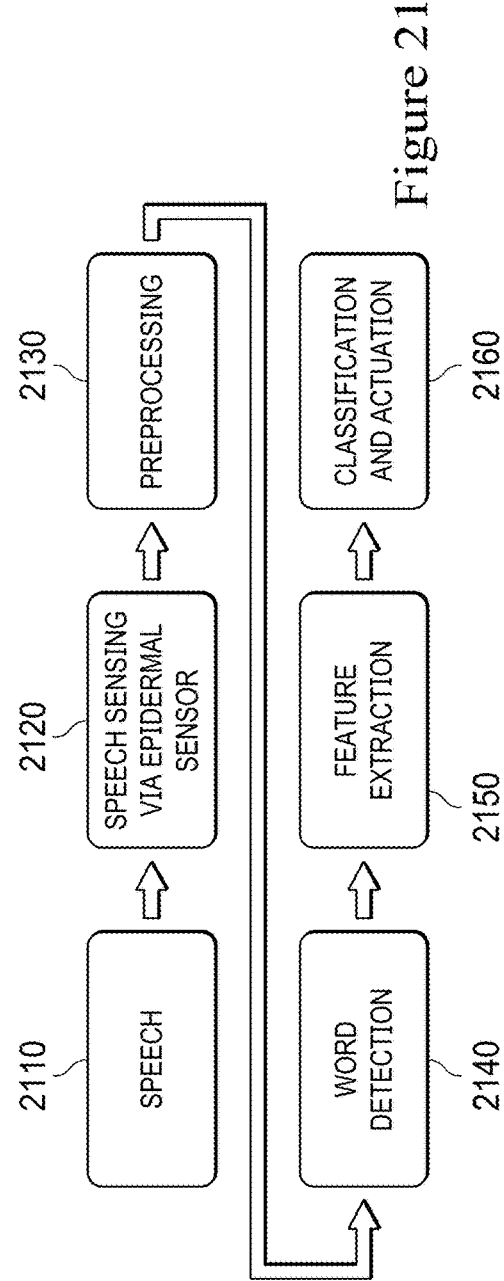
FIG. 21 illustrates an example of a process loop for a speech-based human-machine interface according to some embodiments of the present technology.

A simple isolated word detection system, used in real time to play a Pac-Man game (FIG. 19E), demonstrates the potential of the epidermal acoustic sensor for human-machine interfaces. FIG. 21 shows the signal flow for a control system for the isolated word detection system. Implementation begins with a training phase based on four commands: "left," "right," "up," and "down." As illustrated in FIG. 21, the user (e.g., human patient) speaks and speech monitoring operation (2110) detects the speech using sensing operations (2130) of the conformal epidermal sensor. Preprocessing (2130) involves implementation of noise reduction techniques shown in FIGS. 22A-22F, which does not alter classification accuracy.

Figure 23A:
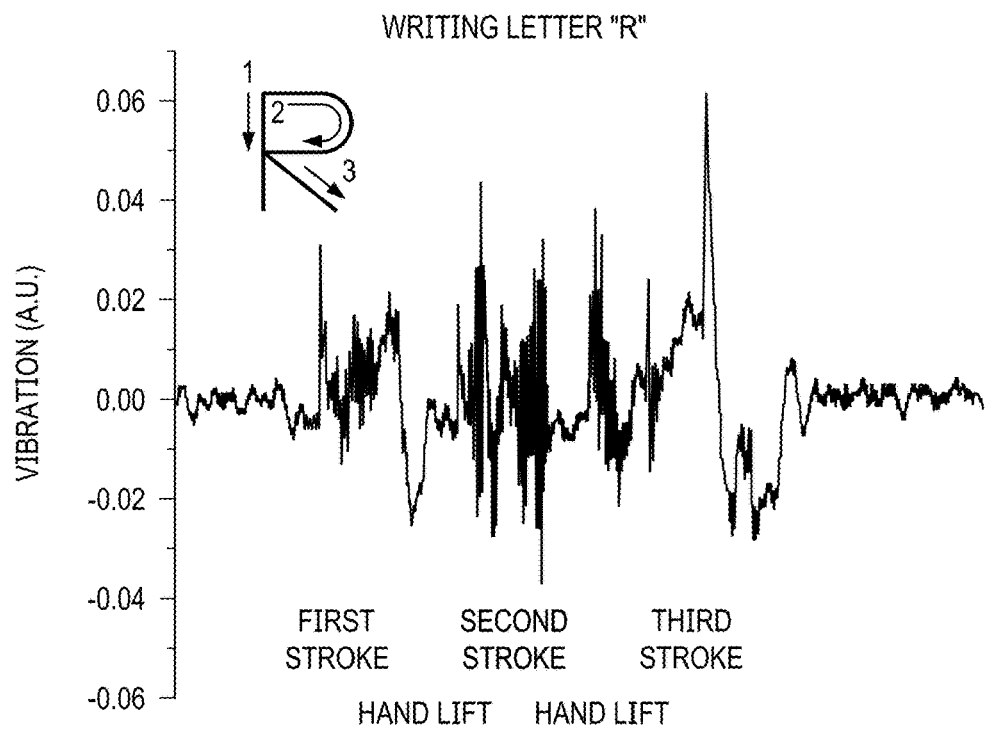
FIGS. 23A-23E illustrate an authentication application where the vibration signal shows distinguishing features when writing.
Figure 23B:
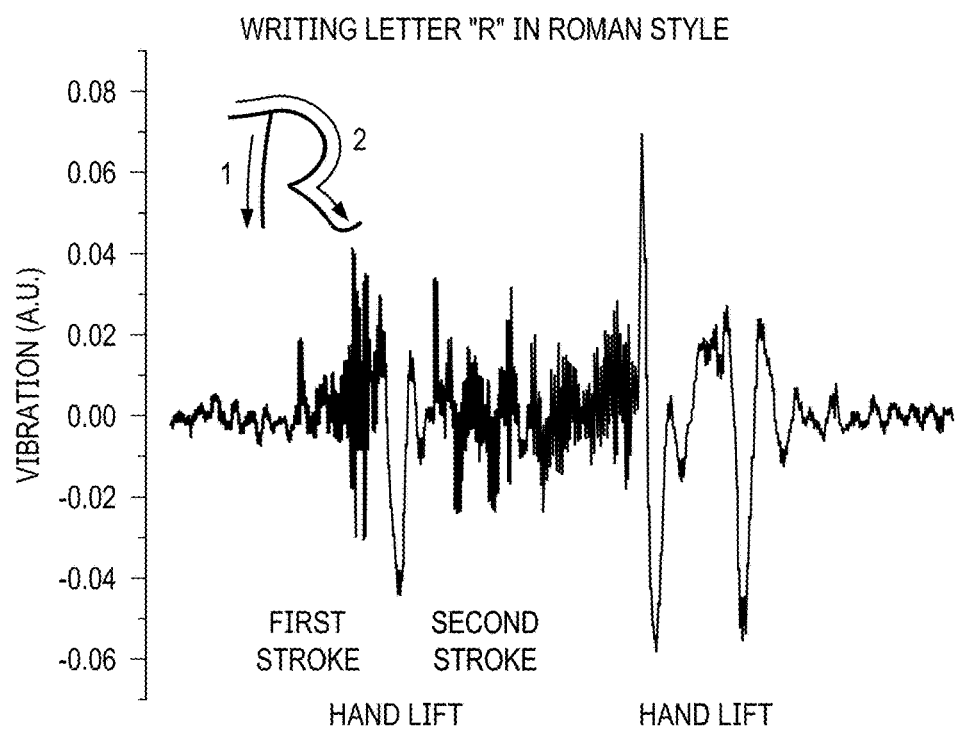
Figure 23C:
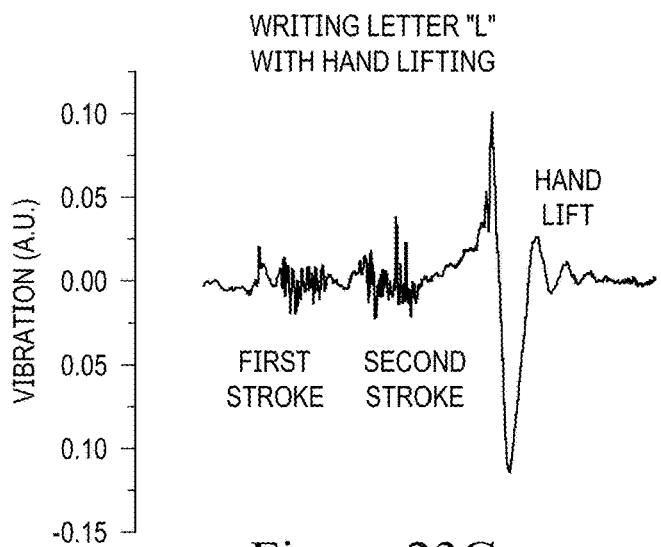
Figure 23D:
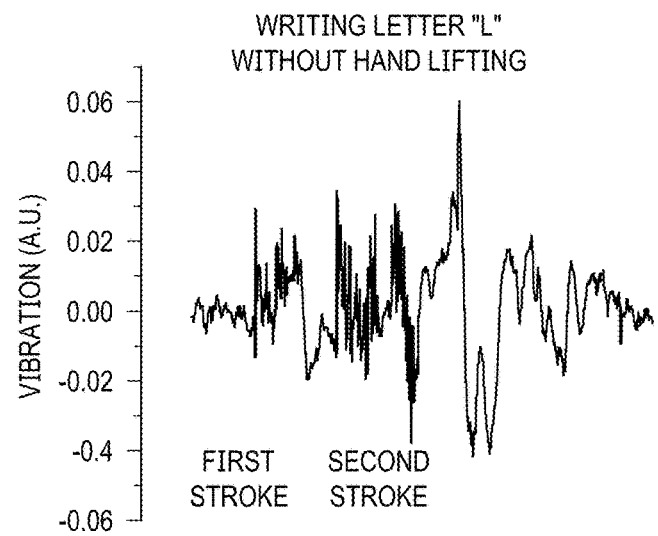
Figure 23E:
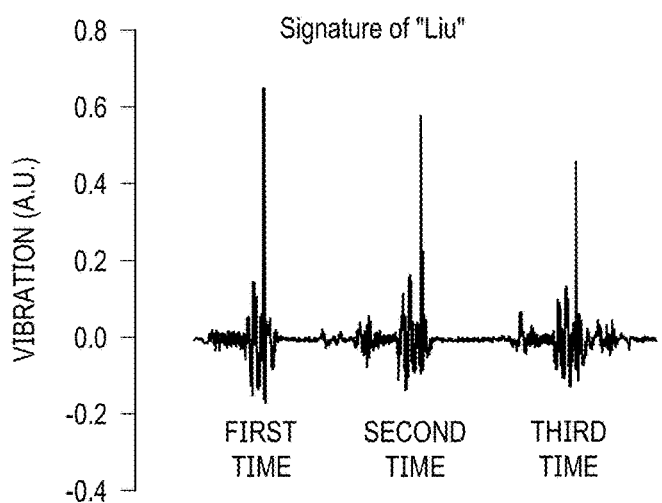
Figure 24A:
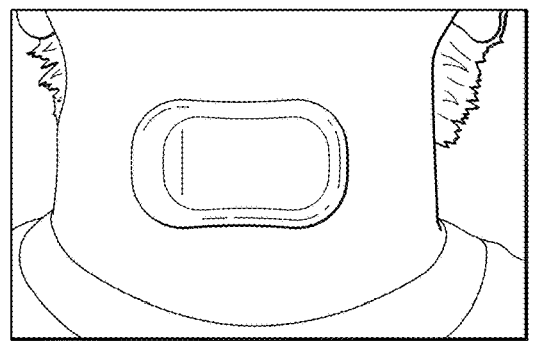
FIG. 24A-24I illustrate a demonstration of wireless speech sensing.
Figure 24B:
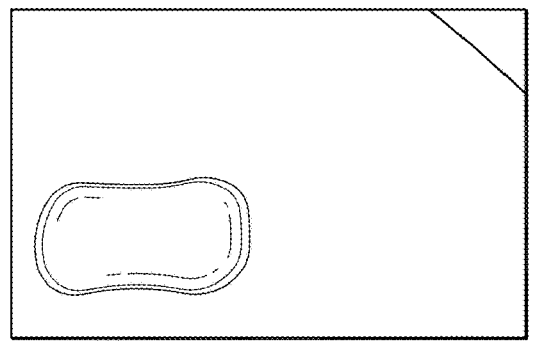
Figure 24C:
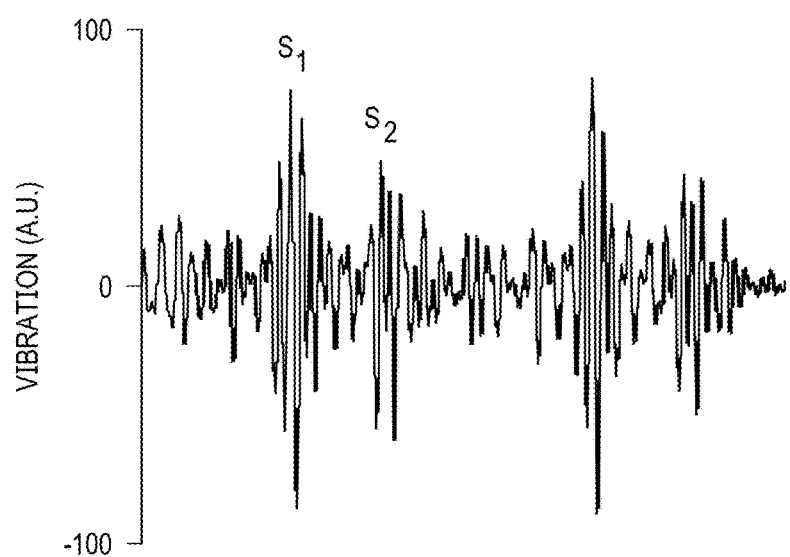
Figure 24D:
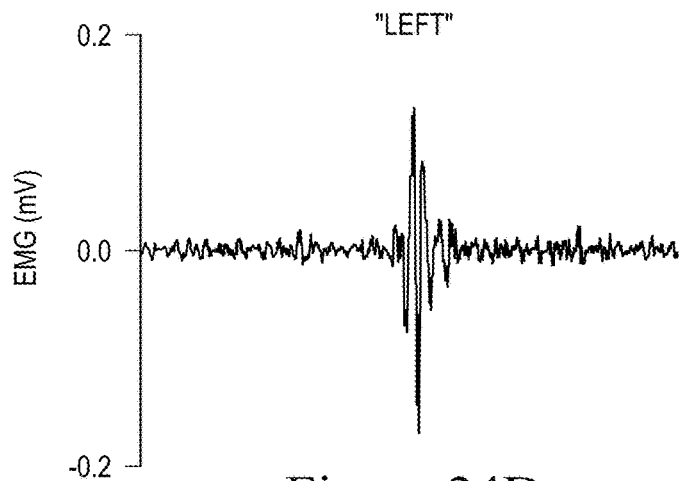
Figure 24E:
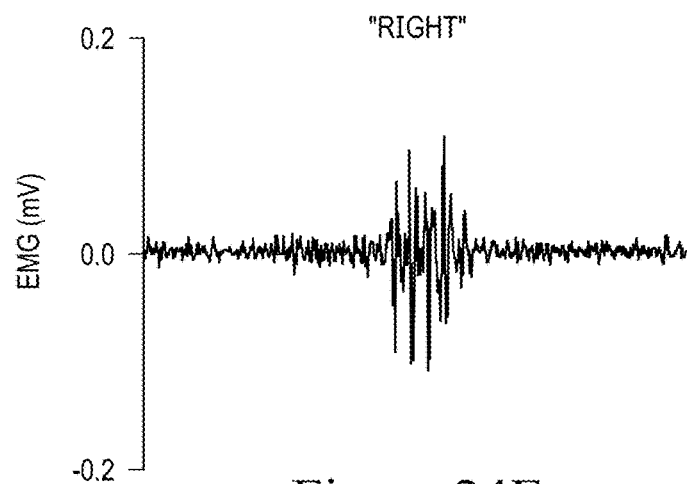
Figure 24F:
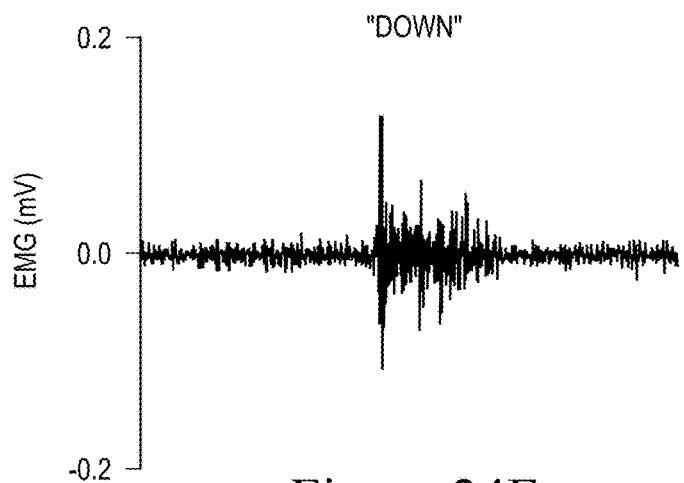
Figure 24G:
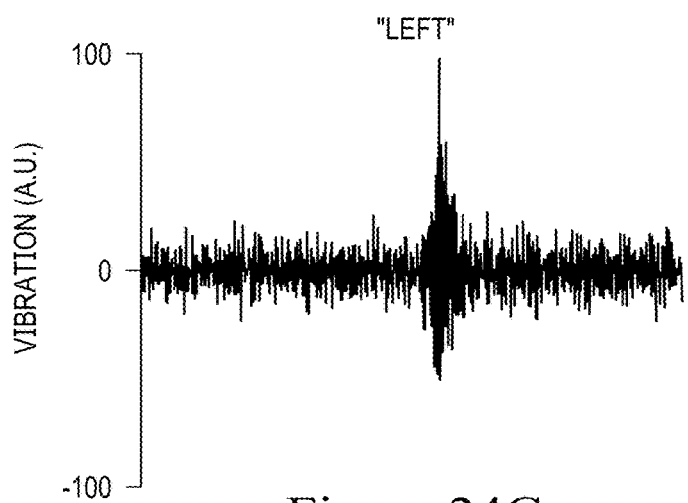
Figure 24H:
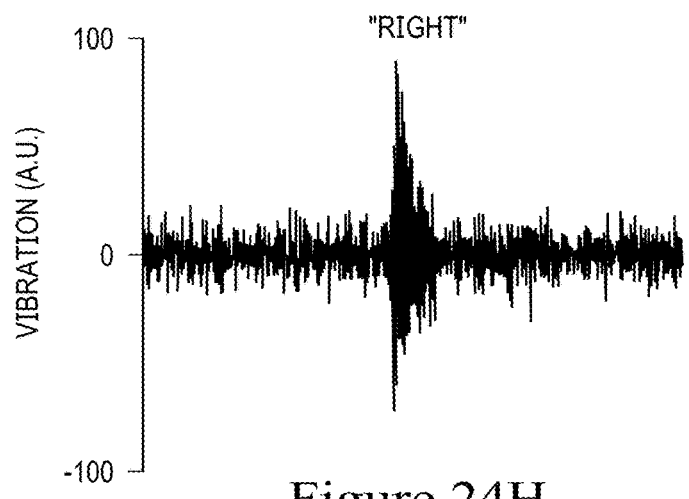
Figure 24I:
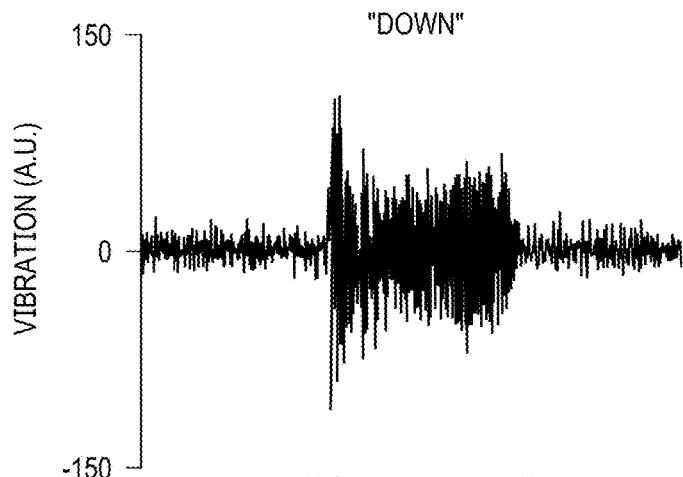

Then word detection operations (2140) and feature extraction (2150) can be performed. Classification (2160) occurs in real time using linear discriminant analysis (LDA). A confusion matrix (FIG. 19D) summarizes the accuracy of this classifier, in which the columns represent the predicted word and the rows represent the targeted word. In this example, the recognition accuracy is 90%. Further improvements are possible through additional training, different classification methods, and a wider passband on the sensor. These same speech recognition strategies can be applied to almost any type of human-machine interfaces, such as drone and prosthesis control. Possibilities in digital authentication appear in FIG. 23A-23E. More specifically, vibration signal shows distinguishing features when writing FIG. 23A letter "R" in normal style, FIG. 23B letter "R" in Roman style, FIG. 23C writing "L" with hand lift, FIG. 23D without hand life, and FIG. 23E signatures.

Discussion

The class of device reported here exploits a thin, lightweight, low modulus, and skin-compatible architecture to enable mechano-acoustic sensing. These physical attributes, although important for wearability and comfort in previous types of "epidermal" technologies, represent critical enabling features for such systems because they allow high-fidelity mechanical coupling across the skin/device interface.

The results create many opportunities in precision recording of sounds and vibratory signatures not only of natural body processes but also of the operation of mechanical implants, such as LVADs. Bench studies and simulation results highlight the fundamental physics associated with this type of sensing. A range of uses with human subjects—in contexts spanning the characterization of heart murmurs in patients known to have either regurgitation or stenosis at defined valvular listening areas (for example, tricuspid or aortic) to machine interfaces in real-time control of computer gaming systems—foreshadows some of the broad opportunities of these concepts. Other potential clinical applications include heart rate variability analysis, beat-to-beat assessment of the pre-ejection period, and left ventricular ejection time. Body sounds, such as snoring, respiration, and gastrointestinal tract movement, are also of some interest. In many cases, fully wireless capabilities in data transfer, on-board data storage/processing, and integrated power supply will be necessary, particularly for applications that require continuous, untethered operation.

Preliminary data (FIG. 24) indicate that the most advanced commercial skin mounted devices with these features (e.g., BioStampRC, MC10 Inc.) offer areal mass densities and low-modulus designs that are sufficient to allow similar levels of mechano-acoustic sensing, as well as multifunctional operation in EP recording. Further optimization of the mechanics and mass distributions associated with this platform, using the design rules outlined here, and further exploration of its use in clinical applications to establish a catalog of pathological functions and conditions represent promising directions for future research.

Fabrication of Epidermal Mechano-Acoustic Device

Figure 25:
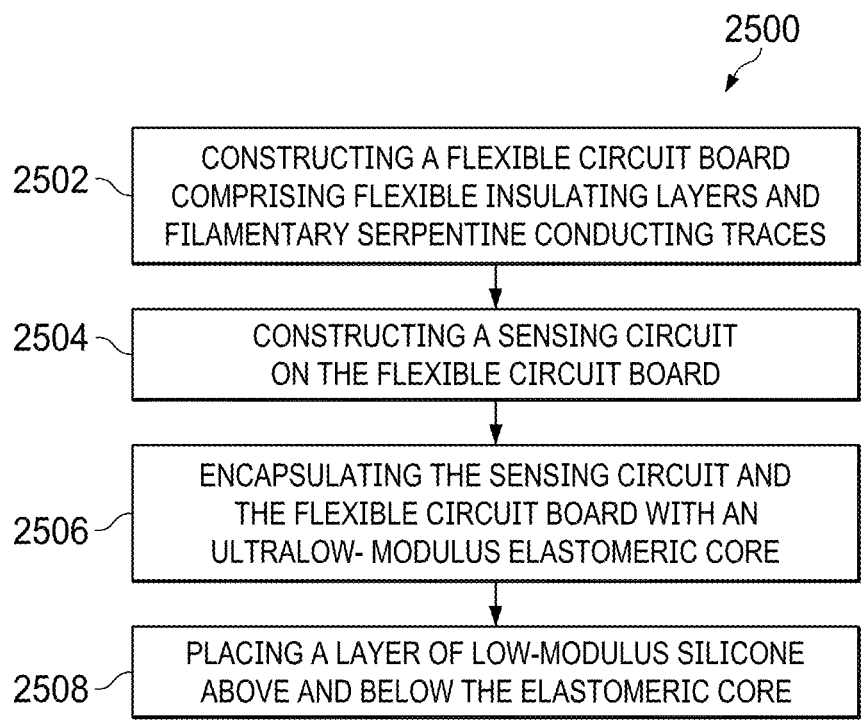
FIG. 25 is a flow chart illustrating an example method for construction of an epidermal mechano-acoustic-electrophysiological measurement device according to some embodiments of the present technology.

FIG. 25 is a flow chart illustrating an example method for construction of an epidermal mechano-acoustic-electrophysiological measurement device according to some embodiments of the present technology. In the embodiments illustrated in FIG. 25, a flexible circuit board comprising a lower flexible insulating layer, filamentary serpentine conducting traces, and an upper flexible insulating layer is constructed, (operation 2502). In some embodiments, the filamentary serpentine conducting traces comprise 3 um thick copper, and the flexible insulating layers comprise polyimide.

A sensing circuit is then constructed on the flexible circuit board, (operation 2504). The sensing circuit comprising: a mechano-acoustic sensor; a low-pass filter coupled with the mechano-acoustic sensor by the filamentary serpentine conductive traces configured to enable sensing of cardiac operation and speech; a high-pass filter coupled with the mechano-acoustic sensor by the filamentary serpentine conductive traces configured to remove motion artifacts; and a preamplifier coupled with the mechano-acoustic sensor by the filamentary serpentine conductive traces through the low-pass filter and the high-pass filter.

The sensing circuit and the flexible circuit board are then encapsulated with an ultralow-modulus elastomeric core, (operation 2506). A layer of low-modulus silicone is placed above and below the elastomeric core, (operation 2508). The low-modulus silicone is configured to function as a mechanical interface to a human subject.

In some embodiments, the fabrication process involves three parts: (i) patterning of the circuit interconnects; (ii) transfer-printing and chip-bonding onto a soft, core/shell substrate; and (iii) covering the top surface with a similar soft core/shell structure. In some embodiments, fabrication of the interconnects can begin with a commercial laminate (e.g., MicroThin, Oak-Mitsui Inc.) that contains a copper carrier film (e.g., 17.5 mm) and a thin copper foil (e.g., 3 mm) separated by a release layer. Spin-coating and thermal curing formed a film of PI (e.g., 1.2 mm; PI 2545, HD MicroSystems) on the side with the thin copper foil (e.g., 3 mm). Peeling this PI-coated layer from the thick copper layer allowed its attachment onto a glass slide coated with poly(dimethylsiloxane) (e.g., sylgard 184, Dow Corning).

The following describes the fabrication process used in some embodiments in more detail: (i) Photolithography and metal etching define a pattern of interconnects in the copper. Another spin-coating and curing process can yield a uniform layer of PI on the resulting pattern. Photolithography and reactive ion etching (e.g., RIE, Nordson MARCH) can be used to define the top and bottom layers of PI in geometries matching those of the interconnects. (ii) A piece of water soluble tape (e.g., Aquasol) can enable the transfer of these encapsulated interconnects onto a trilayer film supported by a silicon wafer, prepared by spin-coating (e.g., 4000 rpm) and curing a thin layer of an ultrasoft silicone (e.g., Silbione, RT Gel 4717 A/B, Bluestar Silicones), followed by a layer of slightly stiffer silicone (e.g., Ecoflex, 00-30, Smooth-On) at 1000 rpm and, finally, another layer of ultrasoft silicone at 1000 rpm.

This trilayer defined the skin-adhesive interface and the core/shell substrate. Removal of the tape by immersion in water can expose the interconnects to allow bonding of the device components onto designated pads using solder paste (e.g., Indalloy 290, Indium Corporation) and a heat gun at ~165° C. (iii) Encapsulation began with manual placement of cured, individual pieces of silicone onto the pads that connect to the ECG electrodes and to those that interface to the ACF cable. Spin-coating (e.g., 1000 rpm) and curing a layer of Silbione followed by a layer of Ecoflex at 1000 rpm defined the core/shell superstrate. Removal of the silicone pieces can complete the fabrication process. Attachment of the ACF cable and ECG electrodes occurred just before mounting the device on the skin.

Device Characterization—Adhesion Strength Tests.

Standard vertical peel measurements defined the adhesion strength between test samples and the skin on the flexor muscle. Each sample (2.5 cm×2.5 cm, 1 mm thick) was prepared by mixing monomer and curing agent components for Silbione and Ecoflex and then thermally curing the materials. The bilayer structure consisted of a 500-mm-thick layer of Ecoflex on a glass substrate, with a 500-mm-thick layer of Silbione on top. The test substrate was placed on the skin, and a corner was attached to the hook of a force gauge at 90° (Mark-10). The reported strength of adhesion corresponds to the measured force divided by the substrate area.

Device Characterization—Water Vapor Transmission Loss Test.

Measurements of water vapor loss follow the standards in ASTM 96-95 (www.astm.org/Standards/E96). Films of Silbione were prepared by spin-coating at 250, 500, 1000, and 2000 rpm on the wafer substrate. Flasks (125 ml) were filled with dry cobalt chloride (Drierite) at equal weight and sealed with the Silbione/Ecoflex films using plastic bands. Changes in weight of each flask were recorded daily for 6 days at room temperature (23° C.) and 50% humidity. The water vapor transmission rates are based on these measurements.

Device Characterization—Cell Viability Assay.

MEFs were obtained from K. Kilian's laboratory. MEFs were isolated from embryos 13 days after coitus with 0.05% Trypsin (Gibco). Cells were cultured in high-glucose Dulbecco's Modified Eagle's Medium (DMEM) (4.5 g/ml) supplemented with 10% fetal bovine serum (Sigma) and 1% penicillin/streptomycin. The medium was changed every 3 days and passaged at 80% confluency.

Device samples were sterilized by autoclaving the samples at 121° C. for 60 min, followed by exposing them to ultraviolet irradiation for 30 min, and finally by washing them in phosphate-buffered saline (PBS). The device surface was exposed to laminin (25 mg/ml; Sigma L2020) in PBS for 30 min and then transferred to a six-well plate. MEFs were seeded on samples at an initial concentration of 20,000 cells/ml and cultured for 5 days. After 1, 3, and 5 days in culture, devices were incubated with Hoechst 33342 (1 mg/ml), calcein AM (2 mM), and ethidium homodimer-1 (4 mM) in PBS solution for 20 min. Samples were mounted onto glass slides and imaged with an IN Cell Analyzer 2000 (GE). Immunofluorescent images were analyzed using ImageJ software. Measurements of cell viability correspond to the proportion of live cells (green) over all cells (green+red). Cells grown on tissue culture plastic in standard DMEM and in DMEM with 10% dimethyl sulfoxide served as positive and negative controls, respectively.

Device Characterization—Vibration Response.

Tests involved attaching the devices, without analog low- and highpass filters, to a flat aluminum stand mounted on a vibration generator (3B Scientific). The vibration was generated by a 1-cm pole connected to the diaphragm of a loudspeaker (e.g., 50 W, 100 mm, 8 ohm; SR 1010, Somogyi) fitted inside a plastic housing. The square wave output of a function generator (e.g., FG100, 3B Scientific) provided a 3-V output to the loudspeaker at discrete frequencies of 1, 5, 10, 50, 100, 250, and 500 Hz. A commercial system (e.g., PowerLab, ADInstruments) enabled data acquisition, without filters, at a sampling rate of 1 kHz.

Measurements of the influence of tissue thickness used fresh chicken breast (e.g., Miller Amish Poultry) sliced into 2 cm×2 cm pieces at thicknesses of 1, 5, 10, and 30 mm. When inserted between the sensor and the vibration stand (4 cm×4 cm), the moist surfaces of the tissue ensured sufficient adhesion to prevent relative movement during vibration, using square waves with an amplitude of 3.7 V and frequencies of 50, 100, 200, 300, 400, and 480 Hz. The effect of mass and tissue thickness was determined using the same experimental setups described above. The sensor was taped firmly to the bottom center of an acrylic box (19 mm×42.5 mm×55 mm, 9.36 g). Medical tape (silicone tape, 3M Medical) wrapped onto the vibration stand stabilized the box on the chicken tissue. Screw nuts (⅜ inch, 1.38 g) were used as elements for added mass, fixed firmly to the top cover of the acrylic box by a double-sided adhesive. Speech sensing was evaluated using a sensor placed in the acrylic box as described above. Measurements involved acoustic vibrations associated with a subject saying "left," with different added masses. The acrylic box was attached to the subject's throat via a double-sided adhesive between the skin and the box interface and medical tape on top of the box. To study the effect of mass location, a set of four mass elements was connected in a column and attached to the middle, upper right, upper left, lower right, and lower left locations of the bottom of the box.

Mechanical Modeling and FEA

3D-FEA simulations based on commercial software packages (Abaqus 6.14, Dassault Systemes) guided the optimization of the mechanics of the system. The elastomers were modeled by eight-node, 3D hexahedron elements (e.g., C3D8R). The electronic chips, serpentine interconnects, and PI layers were modeled by four-node shell elements (S4R).

Displacement boundary conditions applied to the substrate allowed the system to be stretched. The Young's modulus (E) and Poisson's ratio (n) of the materials were as follows: for Silbione, $E_{Silbione}$=5 kPa and $n_{Silbione}$=0.48;

for Ecoflex, EEcoflex=60 kPa and nEcoflex=0.48; for PI, EPI=2.5 GPa and nPI=0.34; and for copper, ECu=119 GPa and nCu=0.35.

FEA using Abaqus also determined the effects of frequency, mass, and tissue thickness on the mechano-acoustic signal. Here, C3D8R were used to model the tissue, the mass objects, and the accelerator, all under a sinusoidal force input. The tissue was modeled as a viscoelastic solid, with a Young's modulus of 0.18 MPa and a Prony series function with constants gi=ki=0.91001 s and ti=0.9899 s. After frequency analysis of the whole system, modal dynamic was chosen as the analysis method to simulate system vibration.

Demonstrations of Seismocardiography

Clinical tests at Camp Lowell Cardiology involved eight elderly patients as volunteers, all providing informed consent. Optimal sensor placement sites at traditional aortic, pulmonary, tricuspid, and mitral locations were determined by ultrasound probes, with verification of heart murmurs by echocardiogram (GE Healthcare). A three-lead setup enabled simultaneous recording of ECG using the same device platform. PowerLab system (e.g., 8/35, ADInstruments) with BioAmp modules served as the hardware for data acquisition and analysis. During measurement, the subject was asked to "stop breathing" for 3 s and then to "breathe normally" after a verbal countdown to eliminate the respiratory effect on the baseline and amplitude of the SCG data. Passing the output of the accelerometer through a 20-Hz low-pass digital filter followed by an analog-to-digital converter in the PowerLab system yielded processed data at a sampling rate of 1 kHz. A band-pass digital filter with a low cutoff and a high cutoff frequency of 1 and 30 Hz, respectively, was used with the ECG signal. All vibration signals were converted from output voltage to "mechano-acoustic response (arbitrary units)."

Measurements from LVADs

The test platform consisted of a closed loop created by connecting a commercial LVAD (e.g., HeartMate II, Thoratec Inc.) and its respective driver by ~1 m of medical grade tubing (e.g., Tygon) at the inlet and outlet, with syringe ports at each location for the introduction of water, without air bubbles. Tape secured the device to the housing of the LVAD. Baseline studies involved measurements of vibration during the operation of the LVAD at various speeds between 8400 and 9400 rpm, with 200-rpm increments. Additional similar experiments used 30% (v/v) glycerol in water. Studies on the effects of VAD thrombosis used fresh blood clots formed via addition of calcium chloride added to 10% (v/v) acid citrate dextrose in fresh bovine whole blood, with the aim of reaching a concentration of 25 mM. Blood clots formed spontaneously during storage overnight at room temperature. Clots with weights of ~250 mg were introduced into the closed loop before activating the LVAD. The sensor response was recorded during circulation of a single clot while operating the LVAD at 9400 rpm. Additional similar experiments used 30% (v/v) glycerol in water.

Algorithms for the Classification of Data Related to Speech

Real-time classification of speech signals relied on a simple four class (left, right, up, and down) isolated word recognition system with a "null" state. Before classification, the data were preprocessed to reduce ambient noise using spectral subtraction and then digitally filtered, using an eighth-order Butterworth filter, from 30 to 1000 Hz. The resulting data were defined as null unless the root mean square value surpassed a threshold. Analyzing the energy of the signal in a sliding 50-ms window enabled determination of the exact onset and offset of the word.

Figure 19D:
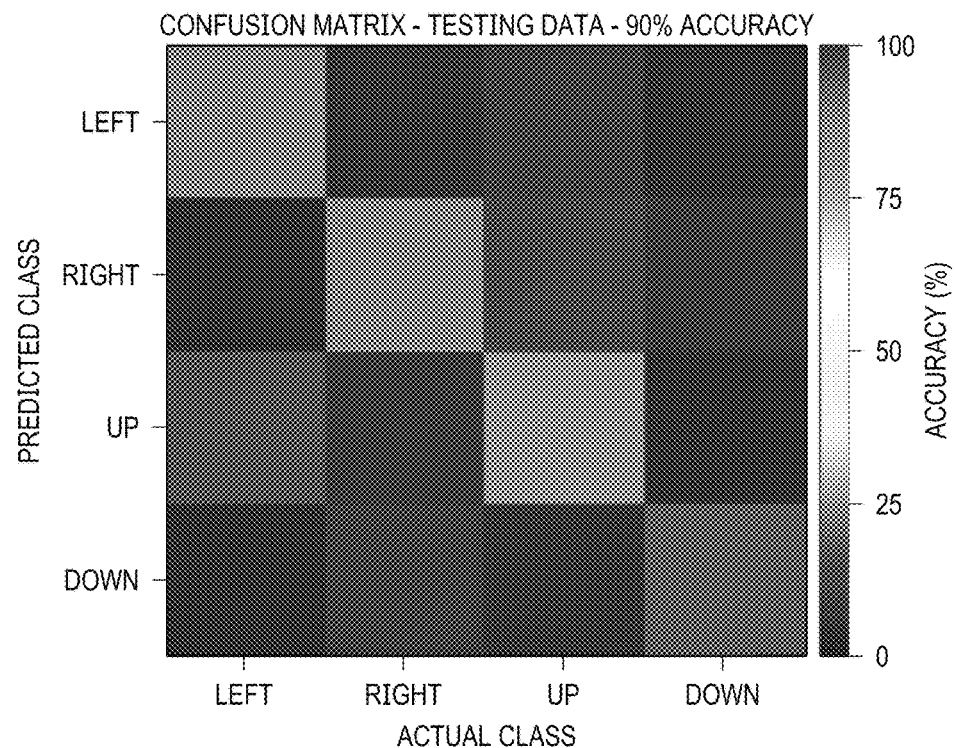
FIG. 19D is a confusion matrix that describes the performance of the speech classification.
Figure 19E:
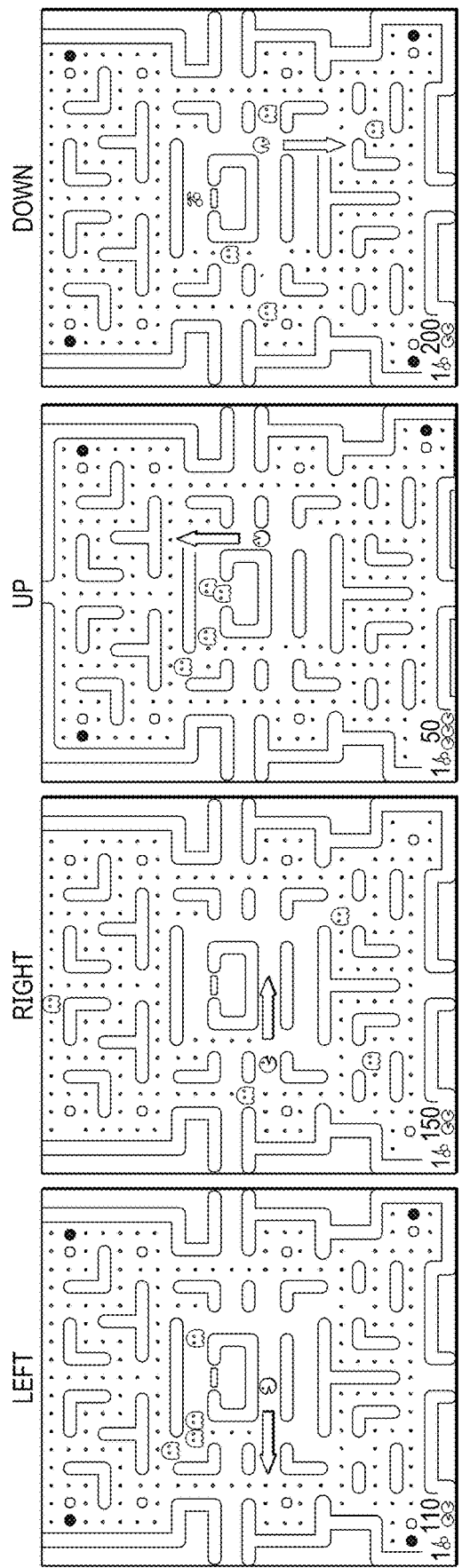
FIG. 19E is a demonstration of speech recognition and classification in a Pac-Man game with left, right, up, and down instruction.

Fourier transformation with a 100-ms time window and a 70-ms overlap defined the time-frequency estimate of the data during the duration of the word. The results were averaged and reduced in dimensionality using principal components analysis to form a feature vector. This feature vector was finally classified using linear discriminant analysis (LDA). Training involved 20 trials from each class, with 90% accuracy (FIG. 19D). The resulting classifier enabled real-time operation in a simple video game (see, e.g., https://pypi.python.org/pypi/pacman-game/ which is herein incorporated by reference in its entirety for all purposes).

Statistical and Data Analysis

Spectra shown in FIGS. 12, 14, and 19 resulted from an FFT algorithm with 1024 window size, Hann (cosine bell) window type, and 50% overlap. For data displayed in spectral power mode, the signal corresponded to an average of three FFTs in frequency domain. All data processing was performed using LabChart 8 (e.g., ADInstruments) and OriginLab 2016 (e.g., Origin).

Computer System

Figure 26:
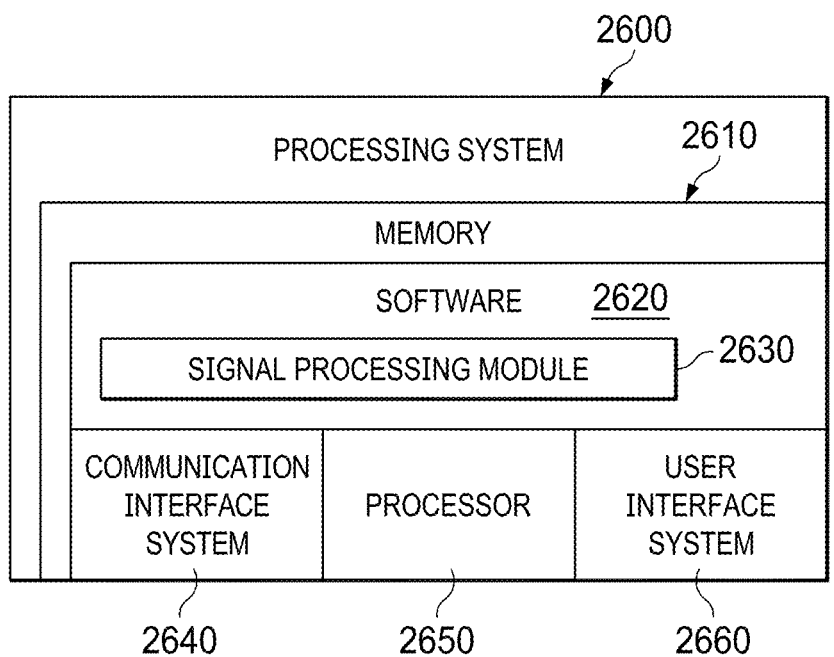
FIG. 26 illustrates an example processing system configured to process outputs of an epidermal mechano-acoustic-electrophysiological measurement device according to some embodiments of the present technology.

FIG. 26 illustrates an example processing system 1800 configured to process outputs of an epidermal mechano-acoustic-electrophysiological measurement device according to some embodiments of the present technology. In some example embodiments an external processing system may be used to receive signals from an epidermal mechano-acoustic-electrophysiological measurement device and process them into desired data formats, graphs, displays, and the like.

FIG. 26 illustrates a set of components within a processing system 2600 that may be used in one or more embodiments of the present technology. Processing system 2600 can include memory 2610 (e.g., volatile memory and/or nonvolatile memory), processor(s) 2650 for executing processing instructions, communication interface system 2640, and user interface system 2660. Memory 2610 can include software 2620 comprising processing instructions, such as signal processing module 2630.

Each of these modules can be embodied as special-purpose hardware (e.g., one or more ASICS, PLDs, FPGAs, or the like), or as programmable circuitry (e.g., one or more microprocessors, microcontrollers, or the like) appropriately programmed with software and/or firmware, or as a combination of special purpose hardware and programmable circuitry. Other embodiments of the present technology may include some, all, or none of these modules and components along with other modules, applications, and/or components. Still yet, some embodiments may incorporate two or more of these modules and components into a single module and/or associate a portion of the functionality of one or more of these modules with a different module. For example, in some embodiments, accelerometer (e.g., 410 in FIG. 4), filters, and amplifier (e.g., 460 in FIG. 4) can be combined into a single device, thus simplifying the construction of various epidermal mechano-acoustic-electrophysiological measurement devices.

Memory 2610 can be any device, mechanism, or populated data structure used for storing information. In accordance with some embodiments of the present technology, memory 2610 can encompass any type of, but is not limited to, volatile memory, nonvolatile memory and dynamic memory. For example, memory 2610 can be random access memory, memory storage devices, optical memory devices, media magnetic media, floppy disks, magnetic tapes, hard drives, SDRAM, RDRAM, DDR RAM, erasable programmable read-only memories (EPROMs), electrically erasable programmable read-only memories (EEPROMs), compact disks, DVDs, and/or the like. In accordance with some embodiments, memory 2610 may include one or more disk drives, flash drives, one or more databases, one or more tables, one or more files, local cache memories, processor cache memories, relational databases, flat databases, and/or the like. In addition, those of ordinary skill in the art will appreciate many additional devices and techniques for storing information which can be used as memory 205.

Memory 2610 may be used to store instructions for running one or more applications or modules on processor(s) 2650. For example, memory 2610 could be used in one or more embodiments to house all or some of the instructions needed to execute the functionality of communications interface system 2640, and/or user interface system 2660. Processing system 2600 may also include an operating system that provides a software package that is capable of managing various hardware resources.

Processor(s) 2650 are the main processors of processing system 2600 used to control the operation an epidermal mechano-acoustic-electrophysiological measurement device, and to process the data received from the device. The volatile and nonvolatile memories found in various embodiments may include storage media for storing information such as processor-readable instructions, data structures, program modules, or other data. Some examples of information that may be stored include basic input/output systems (BIOS), operating systems, and applications.

Communication interface system 2640 can provide an interface for communicating with an epidermal mechano-acoustic-electrophysiological measurement device, and/or other system components.

User interface system 2660 can receive processed data via the processor 2650 operating as directed by signal processing module 2630 and display the processed data to a user through a monitor, speaker, touchscreen, or the like.

Conclusion

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A conformal sensing device for measuring mechano-acoustic recording from skin of a human subject, the conformal sensing device comprising:
    a mechano-acoustic sensor configured to record mechano-acoustic signals generated by a body of a human subject or mechanically active implant;
    a wireless transmitter configured to transmit the mechano-acoustic signals to an external monitoring device; and
    a flexible housing configured to encapsulate the mechano-acoustic sensor and wireless transmitter, the flexible housing comprising an elastomeric core between an upper flexible insulating layer and a lower flexible insulating layer, the elastomeric core having a lower modulus than the upper and lower flexible insulating layers, wherein the flexible housing includes an affixation mechanism configured to allow conformal integration of the conformal sensing device with curvilinear regions of skin of the human subject.

2. The conformal sensing device of claim 1, further comprising one or more electrodes.

3. The conformal sensing device of claim 1, wherein the conformal sensing device has a mass less than five grams and a thickness less than ten millimeters.

4. The conformal sensing device of claim 1, wherein the mechano-acoustic sensor is configured to detect mechano-acoustic signals between 0.01 hertz and ten-thousand hertz, or a limited spectrum of frequencies within 0.01 hertz and ten-thousand hertz.

5. The conformal sensing device of claim 1, wherein the mechano-acoustic signals the mechano-acoustic sensor is configured to record include one or more of temperature, electrophysiological signals, measurement of skin stiffness, quasi-static or dynamic dimensional changes, or voice of the human subject.

6. The conformal sensing device of claim 1, further comprising one or more filters, integrated into the conformal sensing device or located in the external monitoring device, to receive the mechano-acoustic signals from the mechano-acoustic sensor and create processed signals from the mechano-acoustic signals.

7. The conformal sensing device of claim 1, wherein the mechano-acoustic sensor is configured to capture both electromyogram (EMG) signals from articulator muscle groups and acoustic vibrations from vocal cords or to capture electrocardiography (ECG) signals, phonocardiography (FOG) signals, seismocardiography (SCG) signals, or ballistocardiography (BCG) signals from heart activity and respiration.

8. The conformal sensing device of claim 7, wherein the external monitoring device processes the electromyogram (EMG) signals from the articulator muscle groups and the acoustic vibrations from vocal cords to identify speech from the human subject.

9. The conformal sensing device of claim 1, wherein the mechano-acoustic sensor is encapsulated within the elastomeric core.

10. The conformal sensing device of claim 1, wherein the elastomeric core comprises an ultra-low modulus silicone, and wherein the upper and lower flexible insulating layers comprise a low-modulus silicone.

11. The conformal sensing device of claim 10, wherein the ultra-low modulus silicone comprises a Young's modulus E=5 kPa and wherein the low-modulus silicone comprises a Young's modulus E=60 kPa.

12. The conformal sensing device of claim 1 being substantially unaffected by ambient acoustic noise during operation due to the conformal integration with curvilinear regions of skin of the human subject.

* * * * *

UNITED STATES PATENT AND TRADEMARK OFFICE
CERTIFICATE OF CORRECTION

PATENT NO.       : 11,154,232 B2
APPLICATION NO.  : 16/190958
DATED            : October 26, 2021
INVENTOR(S)      : Jae-Woong Jeong et al.

It is certified that error appears in the above-identified patent and that said Letters Patent is hereby corrected as shown below:

In the Claims

Column 24, Claim 7, Line 6, delete "(FOG)" and insert in its place --(PCG)--.

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*